United States Patent
Chang et al.

(10) Patent No.: US 10,087,450 B2
(45) Date of Patent: Oct. 2, 2018

(54) ENGINEERED YEAST FOR PRODUCTION OF ENZYMES

(71) Applicant: Academia Sinica, Taipei (TW)

(72) Inventors: Jui-Jen Chang, Kaohsiung (TW);
Wen-Hsiung Li, Yilan County (TW);
Chieh-Chen Huang, Taichung (TW);
Hao-Yeh Lin, New Taipei (TW);
Ming-Che Shih, Taipei (TW)

(73) Assignee: Academia Sinica, Taipei (TW)

( * ) Notice: Subject to any disclaimer, the term of this patent is extended or adjusted under 35 U.S.C. 154(b) by 3 days.

(21) Appl. No.: 15/156,998

(22) Filed: May 17, 2016

(65) Prior Publication Data
US 2016/0251663 A1    Sep. 1, 2016

Related U.S. Application Data

(63) Continuation-in-part of application No. 13/601,146, filed on Aug. 31, 2012, now Pat. No. 9,340,794.

(60) Provisional application No. 61/529,360, filed on Aug. 31, 2011.

(51) Int. Cl.
| | |
|---|---|
| *C12N 1/15* | (2006.01) |
| *C12N 15/52* | (2006.01) |
| *C12N 15/65* | (2006.01) |
| *C12N 9/42* | (2006.01) |
| *C12N 15/81* | (2006.01) |
| *A01H 5/02* | (2018.01) |

(52) U.S. Cl.
CPC ............... *C12N 15/52* (2013.01); *A01H 5/02* (2013.01); *C12N 9/2437* (2013.01); *C12N 9/2445* (2013.01); *C12N 15/65* (2013.01); *C12N 15/815* (2013.01); *C12Y 302/01004* (2013.01); *C12Y 302/01021* (2013.01); *C12Y 302/01091* (2013.01)

(58) Field of Classification Search
None
See application file for complete search history.

(56) References Cited

U.S. PATENT DOCUMENTS 5,625,126 A    4/1997 Lonberg et al.
8,198,089 B2    6/2012 Akada et al.

2002/0028444 A1    3/2002 Harney et al.
2008/0187983 A1*    8/2008 Dietrich ............... C12N 9/0071
                                                                435/252.33
2008/0293101 A1    11/2008 Peters et al.

OTHER PUBLICATIONS

Bitinaite et al., "USER™ friendly DNA engineering and cloning method by uracil excision", 2007, Nucleic Acids Res 35: 1992-2002.
Gibson et al., "Enzymatic assembly of DNA molecules up to several hundred kilobases", 2009, Nat Methods 6:341-345.
Gibson et al., "One-step assembly in yeast of 25 overlapping DNA fragments to form a complete synthetic *Mycoplasma genitalium* genome", 2008, Proc Natl Acad Sci 105(51):20404-9.
Klock et al., "Combining the polymerase incomplete primer extension method for cloning and mutagenesis with microscreening to accelerate structural genomics efforts", 2008, Proteins 71: 982-994.
Li and Elledge, "Harnessing homologous recombination in vitro to generate recombinant DNA via SLIC", 2007, Nat Methods 4: 251-256.
Li and Elledge, "MAGIC, an in vivo genetic method for the rapid construction of recombinant DNA molecules", 2005, Nat Genet 37: 311-319.
Marsischky and Labaer, "Many Paths to Many Clones: A Comparative Look at High-Throughput Cloning Methods", 2004, Genome Res 14: 2020-2028.
Pachuk et al., "Chain reaction cloning: a one-step method for directional ligation of multiple DNA fragments", 2000, Gene 243:19-25.
Quan and Tian, "Circular Polymerase Extension Cloning of Complex Gene Libraries and Pathways", 2009 PLOS-One 4:6.
Shao et al., "DNA assembler, an in vivo genetic method for rapid construction of biochemical pathways", 2009, Nucleic Acid Res 37:2.
Tsuge et al., "One step assembly of multiple DNA fragments with a designed order and orientation in *Bacillus subtilis* plasmid", 2003, Nucleic Acid Res 31:8.

* cited by examiner

*Primary Examiner* — James S Ketter
(74) *Attorney, Agent, or Firm* — Cesari and McKenna, LLP

(57) ABSTRACT

Described herein is an engineered *Kluyveromyces marxianus* cell, the cell comprising in its genome: (i) two different nucleic acid molecules that each contain a promoter operably linked to a gene encoding a functional enzyme, and (ii) a selection nucleic acid molecule that contains a promoter operably linked to a gene encoding a selectable marker, wherein all of the nucleic acids molecules of (i) and (ii) are in tandem and the engineered cell expresses all of the proteins encoded by the genes of (i) and (ii).

17 Claims, 17 Drawing Sheets

Specification includes a Sequence Listing.

(a)

(b)

(a)

(b)

(a)

(b)

```
                            SEQUENCE LISTING

<160> NUMBER OF SEQ ID NOS: 74

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 1
tagggcctgt ttggcctccc gcggggatc                                         29

<210> SEQ ID NO 2
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 2
tagcactcag tgattattta cgtattcttt gaaatggcag tattgataat gataaactta       60
tacaacatcg aagaagagtc                                                   80

<210> SEQ ID NO 3
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 3
taggccatga cggcagttta tcattatcaa tactgcc                                37

<210> SEQ ID NO 4
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 4
gtagagaatt tcatttttt gtttgtttat gtgtgtttat                              40

<210> SEQ ID NO 5
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 5
ataaacacac ataaacaaac aaaaaaatga aattctctac                             40

<210> SEQ ID NO 6
```

```
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 6
aagatttaaa gtaaattcac gcggccgcct actttcttgc gagacacg                    48

<210> SEQ ID NO 7
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 7
cgtgtctcgc aagaaagtag gcggccgcgt gaatttactt taaatctt                    48

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
agtatggtaa cgaccgtaca ggcaa                                             25

<210> SEQ ID NO 9
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 9
gtagagaatt tcattttttt tgtgtaatat tcttttttt                              40

<210> SEQ ID NO 10
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 10
aaaaaaaaga atattacaca aaaaaaatga aattctctac                             40

<210> SEQ ID NO 11
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 11
aagatttaaa gtaaattcac gcggccgctt acaggcactg agagtagt                    48

<210> SEQ ID NO 12
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 12
```
actactctca gtgcctgtaa gcggccgcgt gaatttactt taaatctt      48

<210> SEQ ID NO 13
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 13
tggtaacgac cgtacaggca agcgcgaagg caaatggaaa agctggtggc ggaaaaaatt    60
catttg    66

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 14
ccagcttttc catttgcctt cgcgcttgcc    30

<210> SEQ ID NO 15
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 15
tcctcgccct tgctcaccat tttatctttt tttagtatag agt    43

<210> SEQ ID NO 16
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 16
actctatact aaaaaaagat aaaatggtga gcaagggcga gga    43

<210> SEQ ID NO 17
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 17
taggccgtcg tggcatgtat gggtttggtt gccagaaaag aggaagtcca tattgtacac    60

<210> SEQ ID NO 18
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 18
taggccacga cggcgtgtac aatatggact cctctttttc    40

<210> SEQ ID NO 19

```
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 19
acgagatcta aaaaatgaa attctct                                            27

<210> SEQ ID NO 20
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 20
tatcccgggt tagtaaagtt tgtaagc                                           27

<210> SEQ ID NO 21
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 21
agggccaaga aggccagccg cggaaattta ggaattttaa ac                          42

<210> SEQ ID NO 22
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 22
taggccacga cggcgtgtac aatatggact tcctcttttc                             40

<210> SEQ ID NO 23
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 23
aaaaagatct gccaccatgg gtaaggaaaa gactc                                  35

<210> SEQ ID NO 24
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 24
aaaaatctag attagaaaaa ctcatcgagc at                                     32

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 25
```
gacatgtgcc agcaaatcca atatc                                         25

<210> SEQ ID NO 26
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 26
cttttccatt tgccttcgcg cttgcctgta cggtcgttac catacttggc ggaaaaaatt    60
catttg                                                              66

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 27
agtatggtaa cgaccgtaca ggcaa                                         25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 28
aagtgttgcc atcgtagcag ttcgt                                         25

<210> SEQ ID NO 29
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 29
acgagatcta tggtgagcaa gggcga                                        26

<210> SEQ ID NO 30
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 30
tatcccgggt tacttgtaca gctcgtcca                                     29

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 31
tccaggtcca gttaatgttc cattc                                         25

<210> SEQ ID NO 32

```
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 32
tatcccgggt tagtaaagtt tgtaagc                                27

<210> SEQ ID NO 33
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 33
caggatcttg ccatcctatg gaact                                  25

<210> SEQ ID NO 34
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 34
tacttggaaa tgctcgtgga atcaa                                  25

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 35
gacatgtgcc agcaaatcca atatc                                  25

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 36
aagtgttgcc atcgtagcag ttcgt                                  25

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 37
cgatctgaag ttcatcaatg gccag                                  25

<210> SEQ ID NO 38
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 38
```
gtgcagatga acttcagggt cagct                                             25

<210> SEQ ID NO 39
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 39
gaacttcaag atccgccaca acatc                                             25

<210> SEQ ID NO 40
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 40
cacattcacc aacatagaat ggatc                                             25

<210> SEQ ID NO 41
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 41
ccgcggggat cgactcataa aatag                                             25

<210> SEQ ID NO 42
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 42
ctactattaa ttatttacgt attctttgaa atggcagtat tgataatgat aaacttatac       60
aacatcgaag aagagtct                                                     78

<210> SEQ ID NO 43
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 43
agtttatcat tatcaatact gccat                                             25

<210> SEQ ID NO 44
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 44
aatcgattta cagaaacttg cacactaaaa atacacaact aaaagcaatt acagttggcg       60
gaaaaaattc atttgtaa                                                     78

```
<210> SEQ ID NO 45
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 45
actgtaattg cttttagttg tgtat                                          25

<210> SEQ ID NO 46
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 46
gcgtctatgt tggaatttga ccccaaaaac catcaattcc ttcgttctaa gccccaagct    60
ttttcgaaac gcagaa                                                    76

<210> SEQ ID NO 47
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 47
agtatggtaa cgaccgtaca ggcaa                                          25

<210> SEQ ID NO 48
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 48
catatacctt tgataccata aaacaagca aatattctta cttcaaacac acccgtggcg     60
gaaaaaattc atttgtaa                                                  78

<210> SEQ ID NO 49
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 49
cgggtgtgtt tgaagtaaga atatt                                          25

<210> SEQ ID NO 50
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 50
aggtaagtat ggtaacgacc gtacaggcaa gcgcgaaggc aaatggaaaa gctggaagct    60
ttttcgaaac gcagaatttt                                                80
```

```
<210> SEQ ID NO 51
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 51
ccagcttttc catttgcctt cgcgcttgcc                                          30

<210> SEQ ID NO 52
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 52
ggaatcccga tgtatgggtt tggttgccag aaaagaggaa gtccatattg tacactggcg         60
gaaaaaattc atttgtaa                                                       78

<210> SEQ ID NO 53
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 53
gtgtacaata tggacttcct cttttc                                              26

<210> SEQ ID NO 54
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 54
gaaatttagg aattttaaac ttg                                                 23

<210> SEQ ID NO 55
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 55
ggggcttaga acgaaggaat tg                                                  22

<210> SEQ ID NO 56
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 56
aatattccct tgatgatatc caactgttgg ttcttgattt cttcagacgg atctcgaata         60
aaaaaatatg cgcatgtgaa                                                     80

<210> SEQ ID NO 57
<211> LENGTH: 25
<212> TYPE: DNA
```

<213> ORGANISM: Artificial Sequence
<220> FEATURE:
<223> OTHER INFORMATION: Synthetic oligonucleotide

<400> SEQUENCE: 57
gagatccgtc tgaagaaatc aagaa                                  25

<210> SEQ ID NO 58
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 58
ccaaaacaat caatttctgg gtgttgaact tctattagta gccgttgata gatctggagc    60
ttccaggggg aaacgc                                            76

<210> SEQ ID NO 59
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 59
agatctatca acggctacta atagaagt                               28

<210> SEQ ID NO 60
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 60
catatacctt tgataccata aaaacaagca aatattctta cttcaaacac acccgttaaa    60
aaatacacat aaattaatgc tagt                                   84

<210> SEQ ID NO 61
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 61
agactaaact ggctgacgga at                                     22

<210> SEQ ID NO 62
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 62
catcaggagt acggataaaa tgc                                    23

<210> SEQ ID NO 63
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 63
tggctccgac agaacaatc                                                19

<210> SEQ ID NO 64
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 64
gtcttgtatg caggactgaa cg                                            22

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 65
acatcaagtt cggacccatt                                               20

<210> SEQ ID NO 66
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 66
ggtaggtccg ggagagctt                                                19

<210> SEQ ID NO 67
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 67
ggcgtcaact ccgtgtgt                                                 18

<210> SEQ ID NO 68
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 68
aggaagcacc aacccagac                                                19

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
cgcttccgtt tacaagaacg                                               20

<210> SEQ ID NO 70

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
aacgttggta gccaaacctc                                               20

<210> SEQ ID NO 71
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 71
gaagctgtaa tggaagaaga tgg                                           23

<210> SEQ ID NO 72
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 72
ctgggaatga aaggaaaatc at                                            22

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
gcgtagattg gaacaacgtg                                               20

<210> SEQ ID NO 74
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 74
agaactaccg gtattgtgtt gga                                           23
```

ENGINEERED YEAST FOR PRODUCTION OF ENZYMES

CROSS REFERENCE TO RELATED APPLICATIONS

This application is a continuation-in-part of U.S. patent application Ser. No. 13/601,146, filed on Aug. 31, 2012, which claims priority to U.S. Provisional Application No. 61/529,360, filed on Aug. 31, 2011. The contents of both prior applications are hereby incorporated herein in their entirety.

BACKGROUND

Synthetic biology is a new approach for design and construction of new biological systems, and for re-design of natural biological systems. To pursue large-scale genomic engineering of a cell, an efficient high-throughput method that can simultaneously introduce many genes into a genome is required.

Various techniques have been developed to enable the assembly of several genes or DNA is modules into larger constructs, such as chain reaction cloning (Pachuk et al., 2000, Gene 243:19-25), ordered gene assembly in *Bacillus subtilis* (OGAB) (Tsuge et al., 2003, Nucleic Acid Res 31:8), DNA assembler in vivo (Shao et al., 2004, Nucleic Acid Res 37:10), uracil-specific excision reagent (USER) cloning (Bitinaite et, al., 2007, Nucleic Acids Res 35: 1992-2002), mating-assisted genetically integrated cloning (MAGIC) (Li and Elledge, 2005, Nat Genet 37: 311-319), sequence- and ligation-independent cloning (SLIC) (Li and Elledge, 2007, Nat Methods 4: 251-256), In-Fusion (Clontech; Marsischky and LaBaer, 2004, Genome Res 14: 2020-2028), polymerase incomplete primer extension (PIPE) (Klock et al., 2008, Proteins 71: 982-994), circular polymerase extension cloning (Quan and Tian, 2009 PLOS-One 4:6), and one-step assembly in yeast (Gibson et al., 2008, Proc Natl Acad Sci 105(51):20404-9; Gibson et al., 2009, Nat Methods 6:341-345). These methodologies are based mainly on historically well-characterized hosts, such as *Escherichia coli, Bacillus subtilis*, and *Saccharomyces cerevisiae*. Other less-studied organisms are still in need of molecular biological tools.

A high demand for cellulosic biofuel is expected in the future. The hydrolysis of cellulose can be better catalyzed by a combination of many cellulases, including endo-β-1,4-glucanases, cellobiohydrolases, cellodextrinases, and exoglucosidases, as the synergism of multiple enzymes can enhance cellulolytic efficiency. One strategy is to engineer yeast strains for producing cocktails of enzymes.

SUMMARY

This invention is based on the discovery of a method, i.e., Promoter-based Gene Assembly and Simultaneous Overexpression (PGASO), that can efficiently insert multiple gene cassettes in a predetermined order into a predetermined site of the genome of a cell. In particular, it was shown that this method can be applied to *Kluyveromyces marxianus*. PGASO is superior to current technologies for genome engineering for at least four reasons: (1) Multiple genes can be transformed into a genome in one single step; (2) Specific upstream promoter sequences are employed for gene assembly in a predesigned order without linker sequences; (3) Gene cassettes with individual promoters can be co-expressed at different expression levels; (4) PGASO is applicable to any host whose genome can be engineered via homologous recombination.

In one aspect, described herein is a method of inserting a plurality of nucleic acid molecules in a predetermined order into the genome of a cell. The method includes providing a plurality of nucleic acid molecules to be inserted into a predetermined site in the genome of a cell in a predetermined order next to each other, the plurality of nucleic acid molecules including a first nucleic acid molecule, a last nucleic acid molecule and at least one intervening nucleic acid molecule to be inserted between the first and last nucleic acid molecules. Each of the plurality of nucleic acid molecules contains (a) a nucleic acid sequence operably linked to a promoter sequence at the 5' end of the nucleic acid molecule, and (b) an overlapping sequence at the 3' end of the nucleic acid molecule, the promoter sequence in each nucleic acid molecule being different. The overlapping sequence in the at least one intervening nucleic acid molecule is homologous to a portion of a promoter sequence in an adjacent nucleic acid molecule and a portion of the promoter sequence in the at least one intervening nucleic acid molecule is homologous to the overlapping sequence in another adjacent nucleic acid molecule. A portion of the promoter sequence of the first nucleic acid molecule is homologous to a first sequence in the predetermined site and the overlapping sequence of the last nucleic acid molecule is homologous to a second sequence in the predetermined site. The plurality of nucleic acid molecules are introduced into the cell, whereby the plurality of nucleic acid molecules join together in the predetermined order via homologous recombination between the overlapping sequences and the promoter sequences, and are inserted into the genome via homologous recombination between the promoter sequence of the first nucleic acid molecule and the first sequence in the predetermined site and between the overlapping sequence of the last nucleic acid molecule and the second sequence in the predetermined site.

The above-described method can be used to engineer a cell for various purposes. For example, the method can be used to design a cell that has certain enzymatic activities. Thus, each of the plurality of nucleic acid molecules can include a nucleic acid sequence encoding an enzyme, e.g., a beta-glucosidase, an endoglucanase, an exoglucanase, a cellubiohyrolase, a protease, a nuclease, an amylase, a laccases, a pectinase, and a lipase.

In another aspect, described herein is an engineered *Kluyveromyces marxianus* cell that contains in its genome (i) two different nucleic acid molecules that each contain a promoter operably linked to a gene encoding a functional enzyme, and (ii) a selection nucleic acid molecule that contains a promoter operably linked to a gene encoding a selectable marker. All of the nucleic acids molecules of (i) and (ii) are in tandem and the engineered cell expresses all of the proteins encoded by the genes of (i) and (ii).

The engineered cell can further include (iii) a reporter nucleic acid molecule that contains a promoter operably linked to a gene encoding a reporter, or (iv) a scaffold nucleic acid molecule that contains a promoter operably linked to a gene encoding a scaffold polypeptide.

The details of one or more embodiments of the invention are set forth in the accompanying drawing and the description below. Other features, objects, and advantages of the invention will be apparent from the description and drawing, and from the claims.

DETAILED DESCRIPTION

Figure 1:
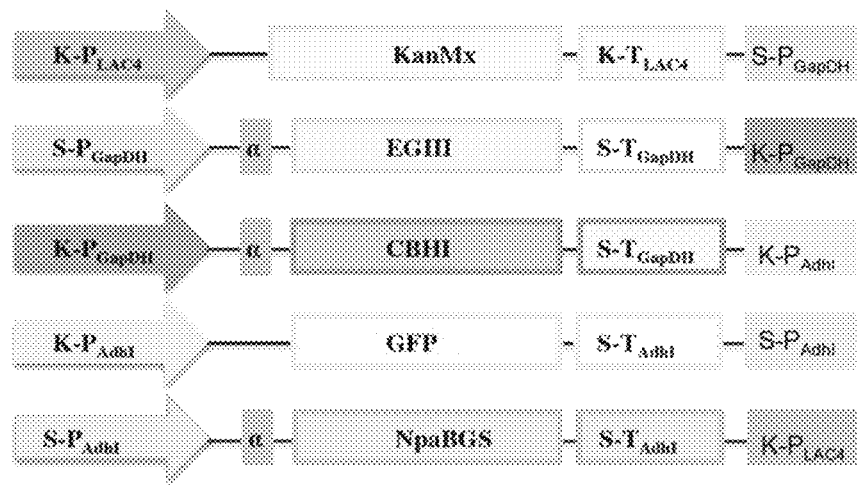
FIG. 1 is a set of schematic diagrams showing (a) exemplary gene cassettes and (b) the genomic integration of 5 gene cassettes in strain KR5.
Figure 1:
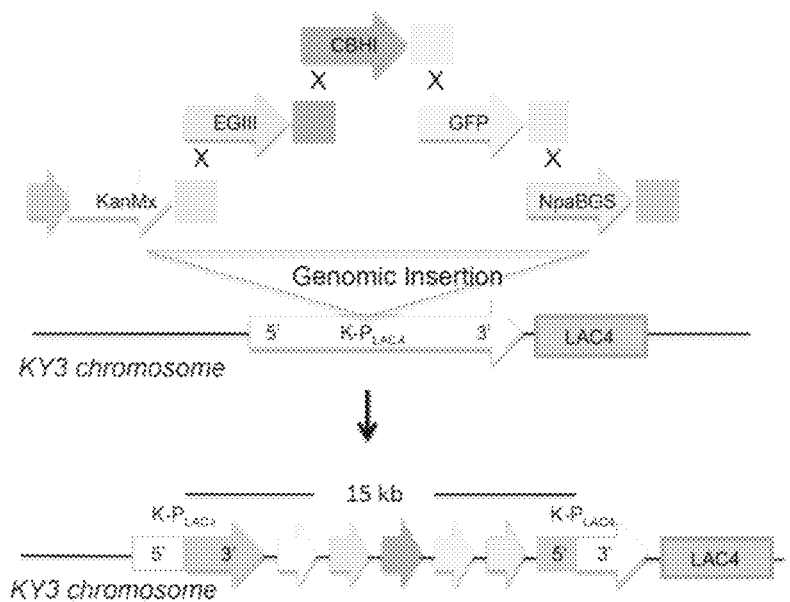

Described herein is a method, i.e., PGASO, for inserting multiple nucleic acid molecules, e.g., gene cassettes, into the genome of a cell in a predetermined order, with a first nucleic acid molecule, a last nucleic acid molecule, and at least one intervening nucleic acid molecule between them. Each nucleic acid molecule contains at least 3 components: (1) a promoter sequence, (2) a gene sequence linked operably at the 5' end to the promoter sequence, and (3) an overlapping sequence at the 3' end of the nucleic acid molecule. See, FIG. 1(a).

A portion of the 5' end of the promoter sequence of the first nucleic acid molecule and a portion of the 3' end of the last nucleic acid molecule are homologous to sequences in a predetermined site in the host genome in order to facilitate site-specific insertion. Each promoter sequence of a nucleic acid molecule is different from the promoter sequences of the other nucleic acid molecules. The overlapping sequence is homologous to a portion of the promoter sequence in the adjacent downstream nucleic acid molecule.

When the nucleic acid molecules are introduced into a cell, they join together in the predesigned order via homologous recombination between the pairs of overlapping and promoter sequences. The joined nucleic acid molecules are inserted into the genome via homologous recombination between a portion of a predetermined genomic site and the promoter sequence of the first nucleic acid molecule, and between another portion of the predetermined genomic site and the 3' overlapping of the last nucleic acid molecule. PSOGA can be applied, for example, in *K. marxianus* for designing optimal enzyme combinations or construction of desired pathways.

The promoter sequence is a nucleic acid sequence that includes a functional promoter. It can also include additional sequences, e.g., an endogenous 5' upstream sequence of the promoter or a sequence heterologous to the promoter. Preferably, the promoter sequence is at or near the 5' end of the nucleic acid molecule. The 5' portions of the promoter sequences preferably do not share significant sequence identity with each other.

In previous studies, a number of promoters have been developed for gene expression systems in *S. cerevisiae*, but very few have been investigated in *K. marxianus*. The wide spectrum of driving strengths observed for different promoters in *K. marxianus* can be further utilized for constructing optimal enzyme combinations or regulating gene expression.

The overlapping sequence can be of any length sufficient to promote homologous recombination, e.g., between 40 and 2000 bases. It is preferably positioned at or near the 3' end of the nucleic acid molecule.

The predetermined site can be anywhere within the genome of a host cell. It can be within a promoter region in the genome. The site can also be a region including sequence repeats. It can also be an exogenous sequence inserted into the genome.

To monitor integration of the nucleic acid molecules into the genome, one of the nucleic acid molecule can include a sequence encoding a selectable marker (e.g., a protein conferring resistance to an antibiotic), and another can include a sequence encoding a reporter protein (e.g., green fluorescent protein). A skilled practitioner would be able to choose suitable selectable markers and reporter proteins.

The method described herein can be applied to any host cell. In particular, it can be used to efficiently engineer *Kluyveromyces marxianus* to express heterologous cellulytic enzymes, as shown in the examples described below.

The PGASO method is a very efficient way to integrate any number of gene cassettes in tandem into the genome of a cell, and to position the gene cassettes in a specific order to achieve a desired expression profile and a specific functional outcome.

Data described below also suggest that the order of the genes and the strength of the promoter linked to a particular gene can be important factors in the formulation of a cellulase cocktail. The order of the genes and the promoter used to drive each gene can be designed such that the enzymes encoded by the genes are expressed in a particular ratio, e.g., more of one specific enzyme than another. Consequently, by changing the order of the genes and matching promoters to genes, the level ratio of the encoded enzymes can be optimized to achieve specific enzymatic activity or specificity.

Accordingly, described herein is an engineered *Kluyveromyces marxianus* strain that contains in its genome at least two different nucleic acid molecules that each include a promoter operably linked to a gene encoding a functional enzyme. The nucleic acid molecules can be inserted into a site of the genome of a host *Kluyveromyces marxianus* strain in a predetermined order using the PGASO method described herein.

Enzymes that can be used to construct engineered strains using the method described herein include those shown in Table 1.

TABLE 1

| Enzyme | Exemplary Source | Gene |
| --- | --- | --- |
| GH5 endoglucanase | *Trichoderma reesei* | egIII |
| GH7 cellobiohydrolase | *Trichoderma reesei* | cbhI |
| GH6 cellobiohydrolase | *Trichoderma reesei* | cbhII |
| GH3 beta-glucosidase | *Neocallimastix patriciarum* | npabgs |
| GH2 endoglucanase | *Aspergillus niger* | eglA (eglA-2) |
| GH12 glucanase | *Aspergillus niger* | egI (eglA-12) |
| cellodextrin transporter | *Neurospora crassa* | cdt-1 |
| AA9 lytic polysaccharide monooxygenase | *Thermoascus aurantiacus* | lpmo |
| cellobiose dehydrogenase | *Myceliophthora thermophila* | cdhI |
| AA9 lytic polysaccharide monooxygenases | *Thermobifida fusca* | lpmo |
| cellulase | *Clostridium thermocellum* | celK |
| exoglucanase | *C. thermocellum* | celS |
| endoglucanase | *C. thermocellum* | celA |
| endoglucanase | *C. thermocellum* | celR |
| xylanase | *C. thermocellum* | xynC |

Promoters that can be used to construct the nucleic acid molecules described herein include those shown in Table 2.

TABLE 2

| Promoter | Source gene |
| --- | --- |
| *S. cerevisiae* GapDHI | TDH1 (glyceraldehyde-3-phosphate dehydrogenase 1) |
| *S. cerevisiae* Adh1 | ADH1 (alcohol dehydrogenase) |
| *S. cerevisiae* PGK | PGK1 (phosphoglycerate kinase) |
| *S. cerevisiae* Adh4 | ADH4 (iron-activated alcohol dehydrogenase) |
| *S. cerevisiae* TDH3 | TDH3 (glyceraldehyde-3-phosphate dehydrogenase 3) |
| *S. cerevisiae* TEF1 | TEF1 (elongation factor 1-alpha) |
| *S. cerevisiae* TPI1 | TPI1 (triosephosphate isomerase) |
| *S. cerevisiae* GAL7 | GAL7 (galactose-1-phosphate uridylyltransferase) |
| *S. cerevisiae* GAL10 | GAL10 |
| *S. cerevisiae* CUP1 | CUP1-1 or CUP1-2 (metallothionein) |
| *S. cerevisiae* ICL1 | ICL1 (isocitrate lyase) |
| *K. lactis* GapDHI | GAP1 (glyceraldehyde-3-phosphate dehydrogenase) |
| *K. lactis* PGK | PGK (phosphoglycerate kinase) |
| *K. lactis* Adh1 | ADH1 (alcohol dehydrogenase) |
| *K. lactis* Lac4 | LAC4 (β-galactosidase) |
| *K. lactis* Adh4 | ADH4 (alcohol dehydrogenase) |
| *C. tropicalis* ICL | ICL1 (isocitrate lyase) |

The engineered strain can further contain a selection nucleic acid molecule that includes a promoter operably linked to a gene encoding a selectable marker. The gene can be a kanamycin resistance gene (kanMX), an aureobasidin A resistance gene (e.g., *S. cerevisiae* AUR1), a Zeocin resistance gene (e.g., *Streptoalloteichus hindustanus* Sh ble), a hygromycin resistance gene (e.g., *Escherichia coli* hph), or a blasticidin resistance gene (e.g., *Borrelia coriaceae* bls).

Other optional nucleic acid molecules include a reporter nucleic acid molecule that contains a promoter operably linked to a gene encoding a reporter (e.g., a green fluorescent protein). The strain can also include in its genome a scaffold nucleic acid molecule that contains a promoter operably linked to a gene encoding a scaffold such as a *C. thermocellum* cellulosomal scaffoldin (e.g., encoded by sdbA, cipA, orf2p, or olpB).

The engineered cell, which expresses a cocktail of enzymes, can be used for various processes. In particular, the engineered cell can be designed to express enzymes for cellulose digestion.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are incorporated herein by reference in their entirety.

EXAMPLE 1

Insertion of Five Gene Cassettes

Materials and Methods (1) Multiple-Gene Cassette Construction

The PGASO method was used to assemble five gene cassettes into *Kluyveromyces marxianus* KY3 strain in a predesigned order. See, FIG. 1. The resultant strain was KR5. In the first gene cassette, the kanMx gene and the *K. lactis* Lac4 promoter fragment from pKlac2 vector (*K. lactis* Protein Expression Kit, New England Biolabs) were amplified and assembled into a fragment using the Lac4-KanMx primers. The coding regions of the second and the third gene cassettes, the *T. reesei* EGIII (endoglucanase) gene and the *T. reesei* CBHI (cellobiohydrolase I) gene, were amplified from cDNA of *T. reesei* and assembled with the ScGapDH promoter and KlPADHI promoter regions by using the ScGapDH-EgIII and the KlGapDH-CBHI primer, respectively, via fusion PCR. The fourth gene cassette with the green fluorescent protein (GFP) gene was constructed using the KlADHI-GFP primers. The fifth gene cassette containing the *N. patriciarum* NpaBGS (beta-glucosidase) gene and a ScADHI promoter were respectively amplified and constructed using the ScADHI-NpaBGS primers. Each gene cassette contains a 46 bp overlapping region with its neighboring cassette on the 3' terminus for recombinatorial gene assembly. PCR was conducted using the TaKaRa Ex Taq system. The primers used are listed in Table 3 below.

TABLE 3

| | Primer name | Sequence |
|---|---|---|
| Cassette construction primers | | |
| Lac4-KanMx | K1-PLac4-3'End-F | 5'-TAGGGCCTGTTTGGCCtcccgcggggatc-3' (SEQ ID NO: 1) |
| | Kl-LAC4_46bpScPGap_Dra3_R | 5'TAGCACTCAGTGATTATTTACGTATTCTTTGAAATGGCAGTATTGATAATGATAAACTTATACAACATCGAAGAAGAGTC-3' (SEQ ID NO: 2) |
| | ScPGapDH-F-BglI | 5'-TAGGCCATGACGGCAGTTTATCATTATCAATACTGCC-3' (SEQ ID NO: 3) |
| | AFEgIII_ScPGapDH_R | 5'-GTAGAGAATTTCATTTTTTTGTTTGTTTATGTGTGTTTAT-3' (SEQ ID NO: 4) |
| ScGapDH-EgIII | ScPGapDH_AFEgIII_F | 5'-ATAAACACACATAAACAAACAAAAAAATGAAATTCTCTAC-3' (SEQ ID NO: 5) |
| | ScTTGap_EgIII_R | 5'-AAGATTTAAAGTAAATTCACGCGGCCGCCTACTTTCTTGCGAGACACG-3' (SEQ ID NO: 6) |
| | EgIII_ScTTGap_F | 5'-CGTGTCTCGCAAGAAAGTAGGCGGCCGCGTGAATTTACTTTAAATCTT-3' (SEQ ID NO: 7) |
| | K1-PGapDH-F | 5'-AGTATGGTAACGACCGTACAGGCAA-3' (SEQ ID NO: 8) |
| | AFCBHI_K1PGapDH_R | 5'-GTAGAGAATTTCATTTTTTTTGTGTAATATTCTTTTTTT-3 (SEQ ID NO: 9) |
| | K1PGapDH_AFCBHI_F | 5'-AAAAAAAAGAATATTACACAAAAAAAATGAAATTCTCTAC-3' (SEQ ID NO: 10) |
| K1GapDH-CBHI | ScTTGap_CBHI_R | 5'-AAGATTTAAAGTAAATTCACGCGGCCGCTTACAGGCACTGAGAGTAGT-3' (SEQ ID NO: 11) |
| | CBHI_ScTTGap_F | 5'-ACTACTCTCAGTGCCTGTAAGCGGCCGCGTGAATTTACTTTAAATCTT-3' (SEQ ID NO: 12) |
| | ScTTGap_K1_PADHI_R | 5'TGGTAACGACCGTACAGGCAAGCGCGAAGGCAAATGGAAAAGCTGGTGGCGGAAAAAATTCATTTG-3' (SEQ ID NO: 13) |
| K1ADHI-GFP | K1-PADHI-F | 5'-CCAGCTTTTCCATTTGCCTTCGCGCTTGCC-3' (SEQ ID NO: 14) |
| | GFPKLADHI-R | 5'-TCCTCGCCCTTGCTCACCATTTTATCTTTTTTTAGTATAGAGT-3' (SEQ ID NO: 15) |
| | KLADHIGFP-F | 5'-ACTCTATACTAAAAAAAGATAAAATGGTGAGCAAGGGCGAGGA-3' (SEQ ID NO: 16) |
| | ScTTGap_46bpScPADHI_CGA-BglI_R | 5'-TAGgccgTCGtggcATGTATGGGTTTGGTTGCCAGAAAAGAGGAAGTCCATATTGTACAC-3' (SEQ ID NO: 17) |
| | ScPADHI_CGA-BglI_F | 5'-TAGgccaCGAcggcGTGTACAATATGGACTTCCTCTTTTC-3' (SEQ ID NO: 18) |
| ScADHI-NpaBGS | NpaBGS-BglII-F | 5'-ACGAGATCTAAAAAAATGAAATTCTCT-3' (SEQ ID NO: 19) |
| | NpaBGS-SmaI-R | 5'-TATCCCGGGTTAGTAAAGTTTGTAAGC-3' (SEQ ID NO: 20) |
| | K1-PLac4 -5'End-R-SfiI | 5'-AGGGCCAAGAAGGCCAgccgcggaaatttaggaattttaaac-3' (SEQ ID NO: 21) |
| | ScPADHI_CGA-BglI_F | 5'-TAGgccaCGAcggcGTGTACAATATGGACTTCCTCTTTTC-3' (SEQ ID NO: 22) |
| Checking primers | | |
| Kan | Kan-BglII-F | 5'-AAAAAGATCTGCCACCATGGGTAAGGAAAAGACTC-3' (SEQ ID NO: 23) |
| | Kan-XbaI-R | 5'-AAAAATCTAGATTAGAAAAACTCATCGAGCAT-3' (SEQ ID NO: 24) |
| | EgIII-1084F | 5'-GACATGTGCCAGCAAATCCAATATC-3' (SEQ ID NO: 25) |
| EgIII | ScTTGap_K1_PGapDH_R | 5'CTTTTCCATTTGCCTTCGCGCTTGCCTGTACGGTCGTTACCATACTTGGCGGAAAAAATTCATTTG-3' (SEQ ID NO: 26) |
| CBHI | K1-PGapDH-F | 5'-AGTATGGTAACGACCGTACAGGCAA-3' (SEQ ID NO: 27) |
| | CBHI-218R | 5'-AAGTGTTGCCATCGTAGCAGTTCGT-3' (SEQ ID NO: 28) |
| GFP | GFP-BglII-F | 5'-ACGAGATCTATGGTGAGCAAGGGCGA-3' (SEQ ID NO: 29) |
| | GFP-SmaI-R | 5'-TATCCCGGGTTACTTGTACAGCTCGTCCA-3' (SEQ ID NO: 30) |
| NpaBGS | NpaBGS-1422-F | 5'-TCCAGGTCCAGTTAATGTTCCATTC-3' (SEQ ID NO: 31) |
| | NpaBGS-SmaI-R | 5'-TATCCCGGGTTAGTAAAGTTTGTAAGC-3' (SEQ ID NO: 32) |
| Internal primers | | |
| amplicon-1 | Kan-673F | 5'-CAGGATCTTGCCATCCTATGGAACT-3' (SEQ ID NO: 33) |
| | EgIII-528R | 5'-TACTTGGAAATGCTCGTGGAATCAA-3' (SEQ ID NO: 34) |
| amplicon-2 | EgIII-1084F | 5'-GACATGTGCCAGCAAATCCAATATC-3' (SEQ ID NO: 35) |
| | CBHI-218R | 5'-AAGTGTTGCCATCGTAGCAGTTCGT-3' (SEQ ID NO: 36) |
| amplicon-3 | CBH-I585F | 5'-CGATCTGAAGTTCATCAATGCCAG-3' (SEQ ID NO: 37) |
| | GFP-150R | 5'-GTGCAGATGAACTTCAGGGTCAGCT-3' (SEQ ID NO: 38) |
| amplicon-4 | GFP-492F | 5'-GAACTTCAAGATCCGCCACAACATC-3' (SEQ ID NO: 39) |
| | NpaBGS-403R | 5'-CACATTCACCAACATAGAATGGATC-3' (SEQ ID NO: 40) |

(2) Yeast Transformation and Clone Screening

The cells were incubated in 5 ml YPD medium (1% Bacto Difco-Yeast Extract, 2% Bacto Difco-Peptone, 2% Merck-D(+)-Glucose) at 30° C., shaking at 250 rpm for 16 hr. To express heterologous enzymes in KY3, a transformation method of *K. lactis* was employed (Colussi and Taron, 2005, Appl Environ Microbiol (71):7092-7098). The target DNA fragments in a 5 µg volume with an equal molar ratio of each fragment were mixed with 40 µl competent cells. The electroporation was performed (1.0 kV, 400Ω, and 25 µF capacitance) in BioRad system (GenePluser Xcell™, Bio-Rad, Hercules, Calif.) with an aluminum cuvette (2 mm). The cells were spread onto YPG plates (1% Bacto Difco-Yeast Extract, 2% Bacto Difco-Peptone, and 2% Merck-galactose) containing kanamycin (20 µg/mL). To confirm the presence and the desired order of each fragment, each isolated colony was digested in QucikExtract™ DNA Extraction Solution (EPICENTRE, Madison, Wis.) to remove yeast cell wall and examined by PCR with specific primer pairs. See "checking primers" in Table 1. To verify by PCR that these gene cassettes were inserted and assembled in the correct order, gene specific internal primers for each cassette were designed and used. See, Table 1. These clones were further observed under bright field microscope with phase contrast and fluorescence with a GFP filter, and photographed by a confocal microscope and single molecule detection system (Leica TCS-SP5-MP-SMD, Germany).

(3) Quantitative PCR Analysis

The cells of each isolate were incubated in YPG medium containing kanamycin (20 μg/mL) at 30° C., 200 rpm for 16 hr. The template mRNA was then purified from yeast cells using an RNeasy Protect mini kit (High Pure RNA Isolation Kit, Roche). cDNA synthesis was performed with a reverse transcription kit (SuperScript™ II kit, Invitrogen). The relative quantification of each gene was carried out via the Universal Probe Library Set (LightCycler® 480 Probes Master, Roche) with a specific primer pair (the amplicon size was 100 to 150 bp) on a LightCycler (LightCycler® 480, Roche), following the protocol of the manufacturer.

(4) Quantitative Assays of Enzyme Activities

The supernatants of yeast cultures were used in several glucanase activity assays, each with different test substrates. Total glucanase activity was assayed by mixing 40 μl supernatant of with 60 μl buffer solution (50 mM 4-methylumbelliferyl-β-D-cellobiopyranoside (MUC), 50 mM sodium acetate, pH 3). Release of 4-methylumbelliferone (MU) with fluorescence units (FU) was measured by a fluorescent intensity reader (SpectraMax M2, MDS) with the excitation at 365 nm and emission at 465 nm. Exo-glucanase and endo-glucanase activities were assayed by mixing 40 μl supernatant with 60 μl buffer solution containing either 2% phosphoric acid-swollen cellulose (PASC) or 2% CM-cellulose. The amount of reducing sugar was measured using the Somogyi-Nelson method to determine the number of glucose equivalents. The quantitative assay of β-glucosidase activity used was similar to the above method, but 50 mM p-nitrophenyl-D-glucose (pNP-Glc) was used as substrate and the detection was done with luminescence under 410 nm UV light. Protein concentration was determined by the Bradford method.

(5) Carbon Source Utilization and Ethanol Production Assay

The transformed yeast cells were grown on 2% agar YP medium plates with cellobiose, β-glycan, CMC, or PASC as carbon source individually. The same recipe in liquid medium was also used for yeast growth and ethanol fermentation. The productivity of ethanol was analyzed by gas chromatography (Shimadze GC-14, Japan) with a flame ionization detector (FID) and a stainless steel column (80/120 Carbopack B/6.6% Carbowax, 2 m×2 mm), with nitrogen as the mobile gas. The running condition included heating of the column from 80 to 150° C. at a ramp rate of 4° C. per min, an injection temperature of 180° C., and a detection temperature of 250° C. Each fermentation experiment and the subsequent analysis were repeated three times.

Results (1) Insertion of Five Gene Cassettes

To confer the hydrolysis ability of K. marxianus KY3 on higher order carbon sources such as cellulose, three cellulase genes, as well as a selecting marker and a reporter gene, were introduced into the KY3 genome. The three cellulase genes were a beta-glucosidase gene (NpaBGS) originally found in a cow rumen fungus, i.e., N. patriciarum, and two T. reesei cellulase genes, i.e., the EGIII and the CBHI gene.

The neomycin phosphotransferase gene essential for kanamycin resistance, i.e., the KanMX gene, was used as a marker gene for clone screening. The green fluorescent protein (GFP) gene was employed as a promoter reporting system and as a bio-sensor to monitor cell state. The five genes were assembled as one single cassette for genetic manipulation via recombinationary insertion. To avoid unexpected recombination events in multi-gene integration into similar regions, various heterologous promoters with low homologous sequences were used. An ideal promoter preferably had certain properties, e.g., high strength, low background, rapid induction, and simple induction conditions. Several constitutive promoters that fulfill these conditions were chosen for the five-gene cassettes. These promoters included ScPGapDH (the GapDHI promoter) and ScPADHI (the AdhI promoter) from S. cerevisiae, and KlPGapDH and KlPADHI from K. lactis, which showed only 40-55% sequence identity between each other in the 5' upstream region.

Transformation of five gene cassettes in a single step into the genome of K. marxianus KY3 was achieved. The first gene cassette included a selection marker gene (the KanMX gene, 810 bp) linked with a portion of the PLac4 promoter. In the second gene cassette, an endoglucanase gene (the EGIII gene, 1449 bp) was linked with the KlPGapDH promoter. An exoglucanase gene (the CBHI gene, 1749 bp) driven by the KlPGapDH promoter was used in the third gene cassette. The fourth gene cassette contained a reporter gene (the GFP gene, 720 bp) as well as the ScPADHI promoter. In the last gene cassette, a beta-glucosidase gene (the NpaBGS gene, 2526 bp) was linked with the KlPADHI promoter. These five gene cassettes were prepared by PCR, with a 46 bp overhang to the 5' end of each promoter and a 46 bp overhang to the 3' end of the terminator region. See, FIG. 1, (a).

The overhangs were designed to facilitate homologous recombination, because the 5' end of each fragment overlaps with the 3' end of its 5' upstream neighbor; the 5' overhang of the first cassette (the KanMX gene) and the 3' terminal on the last cassette (the NpaBGS gene) overlap with the LAC4 promoter region in K. marxianus KY3. See, FIG. 1, (a). Consequently, the five gene cassettes, each with an independent promoter, alpha factor from K. lactis, gene coding region, and a terminator, were assembled in the predesigned order, i.e., Kan-EGIII-CBHI-GFP-NpaBG, as a 14877 bp DNA fragment. The fragment was integrated into the LAC4 promoter region of K. marxianus KR3 via single-step genome recombination, resulting in strain KR5. See, FIG. 1, (b). Strain KR5 was selected with kanamycin resistance. The activation of green fluorescent protein via promoter ScPA-DHI was confirmed by fluorescence microscopy.

The five-gene insertion in KR5 was confirmed by PCR with five pairs of gene specific internal primers (see Table 1). To verify that these gene cassettes were assembled in the correct order, four internal primer pairs spanning the gap regions of each cassette were designed (see Table 1) and used in PCR. The one-step multi-gene fragment assembly method has thus been successfully demonstrated in KR5.

Figure 2:
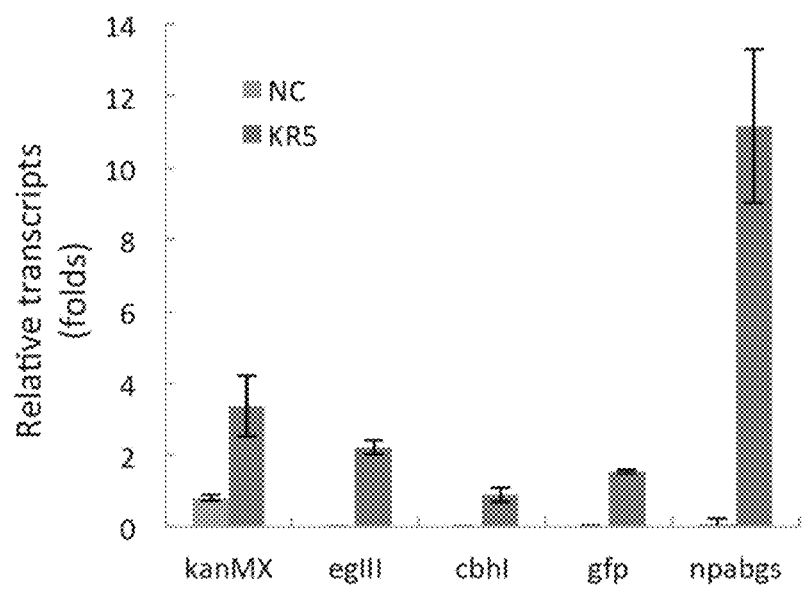
FIG. 2 is a set of bar graphs showing (a) the relative ratios of the transcripts of various genes and (b) the copy numbers of the genes in *K. marxianus* strains NC and KR5.
Figure 2:
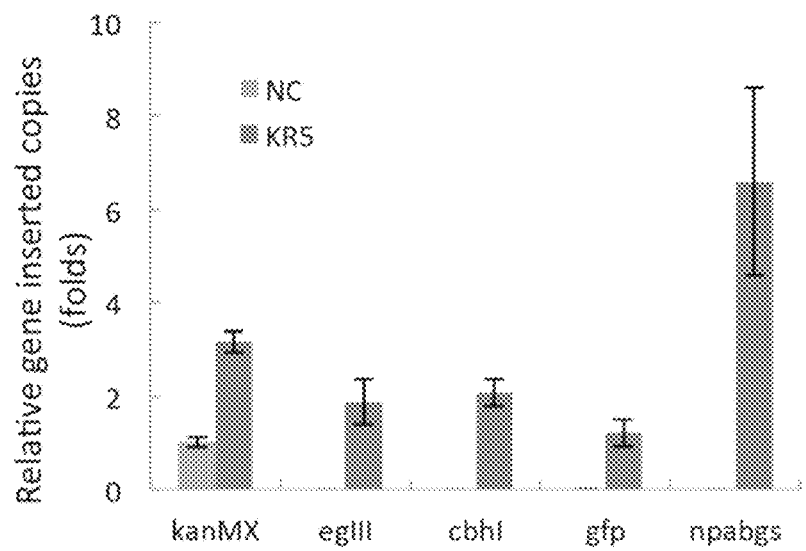

In addition, genomic DNA and total RNA were isolated from KR5 and the control strain NC (KY3 transformed with a vector containing the KanMX gene) for quantitative PCR analysis, which was performed with 5 gene-specific primer sets using the UPL system. The relative gene expression levels of the five genes in KR5 were about 3 (kan), 2 (egIII), 1 (cbhI), 1.5 (gfp) and 11 (NpaBGS) folds higher relative to the expression level of actin. See, FIG. 2(a). Similarly, the observed inserted copy number ratios of the five genes in the isolates relative to the endogenous actin gene were approximately 3 (kan), 2 (egIII), 2 (cbhI), 1.5 (gfp) and 6 (NpaBGS). See, FIG. 2, (b). The data indicated unequal gene copy numbers and transcript abundances among the five genes. The differences might have been caused by non-specific gene insertions and varying transcription efficiencies among different promoters. A comparison of the transcript abundances with the inserted copy numbers suggests that, in KR5, the GapDHI promoter from *K. lactis* was weakeast and the AdhI promoter from *S. cerevisiae* was the strongest promoters among the constitutive promoters used in this study.

All promoters used here were derived from strong constitutive genes associated with yeast-specific metabolic pathways. The use of this type of promoter is advantageous, as the engineered strains can be driven under normal growth, on different carbon sources, or under a high cell density immobilization condition. Moreover, the wide spectrum of induction strengths observed in different promoters may be drawn upon to devise efficient gene expression systems for optimal enzyme-cocktails or to study gene regulation in yeast.

This study shows that assembling specific sequences using over-lapping fragments is feasible and that PSOGA can be tailored for various purposes via promoter design. It also shows that KY3 is a great host for multi-gene assembly and genome engineering via synthetic biology.

(2) Characterization of the Secreted Cellulases of KR5

To quantify the secreted cellulase activities, the supernatant of KR5 was harvested for analysis without protein purification. The commercial cellulolytic enzyme mixture kits Celluclase 1.5 L and Nova188 were used as benchmarks. The supernatant with KR5 secreted cellulases and diluted commercial enzymes were estimated using an equal MUC activity which represented the total glucanase activity.

Figure 3:
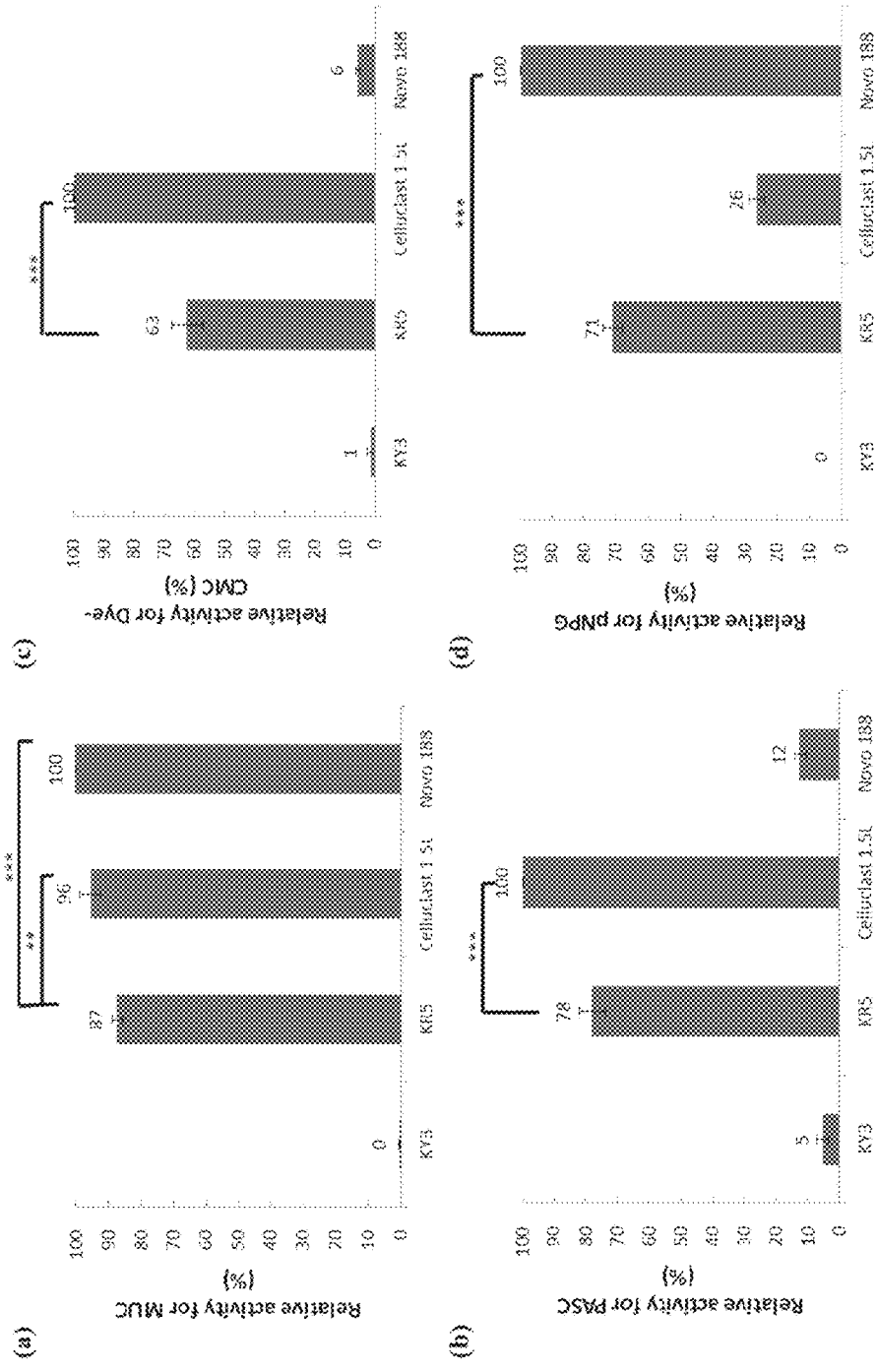
FIG. 3 is a set of bar graphs showing the cellulolytic enzyme activities in the supernatant of KR5 culture as compared to those of *K. marxianus* strain KY3 and commercial cellulolytic enzyme mixture kits, i.e., Celluclast 1.5 L and Novozyme 188. The relative activities were assessed using (a) MUC, (b) Dye-CMC, (c) PASC, and (d) pNPG as the substrate, respectively. The protein concentration in the supernatant of the *K. marxianus* cultures was 1.3 mg/ml. *: P<0.05 (significant), : P<0.01; *: P<0.001; N.S., non-significant.

The MUC activity assay was performed with MUC as the substrate, and the results indicated that the MUC activity in the supernatant of KR5 was equivalent to those of 0.5 unit of Celluclast 1.5 L and 1 unit of Novozyme 188, and higher than that of the control strain (i.e., KY3). See, FIG. 3, (a). The glucose assay indicated significantly improved digestion of PASC by KR5; the activity was up to 80% of that of the 0.5 unit of Celluclast 1.5 L. See, FIG. 3, (b). The activity assay with Dye-CMC as the substrate suggested that the endo-glucanase activity in the supernatant of KR5 was significantly improved due to the EGIII secreted by KR5; the activity was 60% of the 0.5 unit of Celluclast 1.5 L. See, FIG. 3, (c). The activity assay with pNPG as the substrate showed that the beta-glucosidase activity of NpaBGS in the supernatant of KR5 was higher than that of the control strain, and the activity was nearly 80% of 1 unit of Novozyme 188. See, FIG. 3, (d). These data demonstrate successful co-expression of the exogenous fungal genes and secretion of their gene products without any significant post-translational modification problems.

Successful protein production in a heterologous host at a commercial scale often requires the regulation of the timing and the expression level of the cloned gene(s). The long culturing time required by fungi is a current bottleneck of traditional enzyme purification technologies, such as Celluclast 1.5 L for *Trichoderma* and Novo188 for *Aspergillus*. The faster growth rate of *K. marxianus* makes it more desirable for commercial applications. In this study, the promoters described above and the signal sequence of the *K. lactis* alpha-mating factor were used to express and secrete heterologous cellulases in KR5, at a much higher efficiency than the classical *S. cerevisiae* system. Furthermore, the new host strain *K. marxianus* KR5 is not only naturally competent to secrete enzymes, but also efficient for combining different enzyme systems for downstream processing of industrial enzymes.

(3) Sugar Utilization and Ethanol Production of KR5

Figure 4:
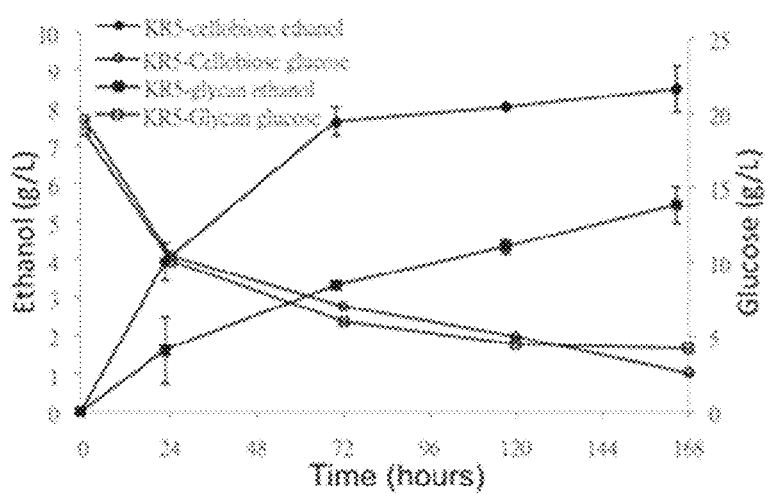
FIG. 4 is a set of two graphs showing the fermentation ability of KR5.
Figure 4:
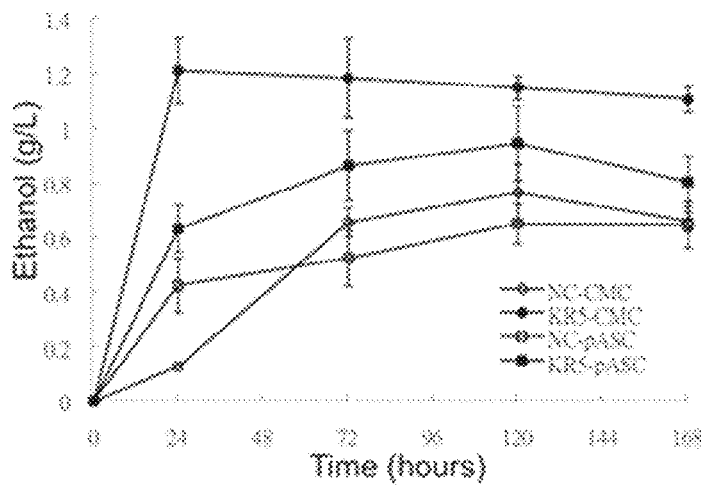

Several types of cellulose were tested in this study to determine the carbon source utilization and ethanol fermentation abilities of KR5, KY3-196, which is a KY3 strain transformed with the NpaBGS gene, and the control strain NC. All three strains were capable of utilizing glucose and cellobiose for growth, but only KR5 can, additionally, assimilate beta-glycan and CMC. To examine the SSF ability of KR5, fermentation was performed in YP medium containing cellobiose, beta-glycan, CMC, or PASC as the sole carbon source. After cultivation of cells in YPD medium for 24 h at 30° C., the cells with O.D. 20 were harvested for subsequent inoculums. KR5 could use cellobiose, beta-glycan, CMC or PASC as the sole carbon source for fermentation. The efficiency of cellobiose conversion with KR5 was as good as its glucose utilization, where it produced 8.5 g/L ethanol with a 93% conversion ratio in 168 h at 37° C. See, FIG. 4, (a). When 2% beta-glycan was the sole carbon source, KR5 produced 5.4 g/L ethanol with a 74% conversion ratio in 168 h at 37° C. See, FIG. 4, (a). These data indicated that KR5 could express cellulolytic enzymes and directly produce ethanol from cellulosic materials. The CMC and PASC assimilation abilities were only moderately increased compared to the control strain. See, FIG. 4, (b).

EXAMPLE 2

Insertion of Seven Gene Cassettes

Figure 5:
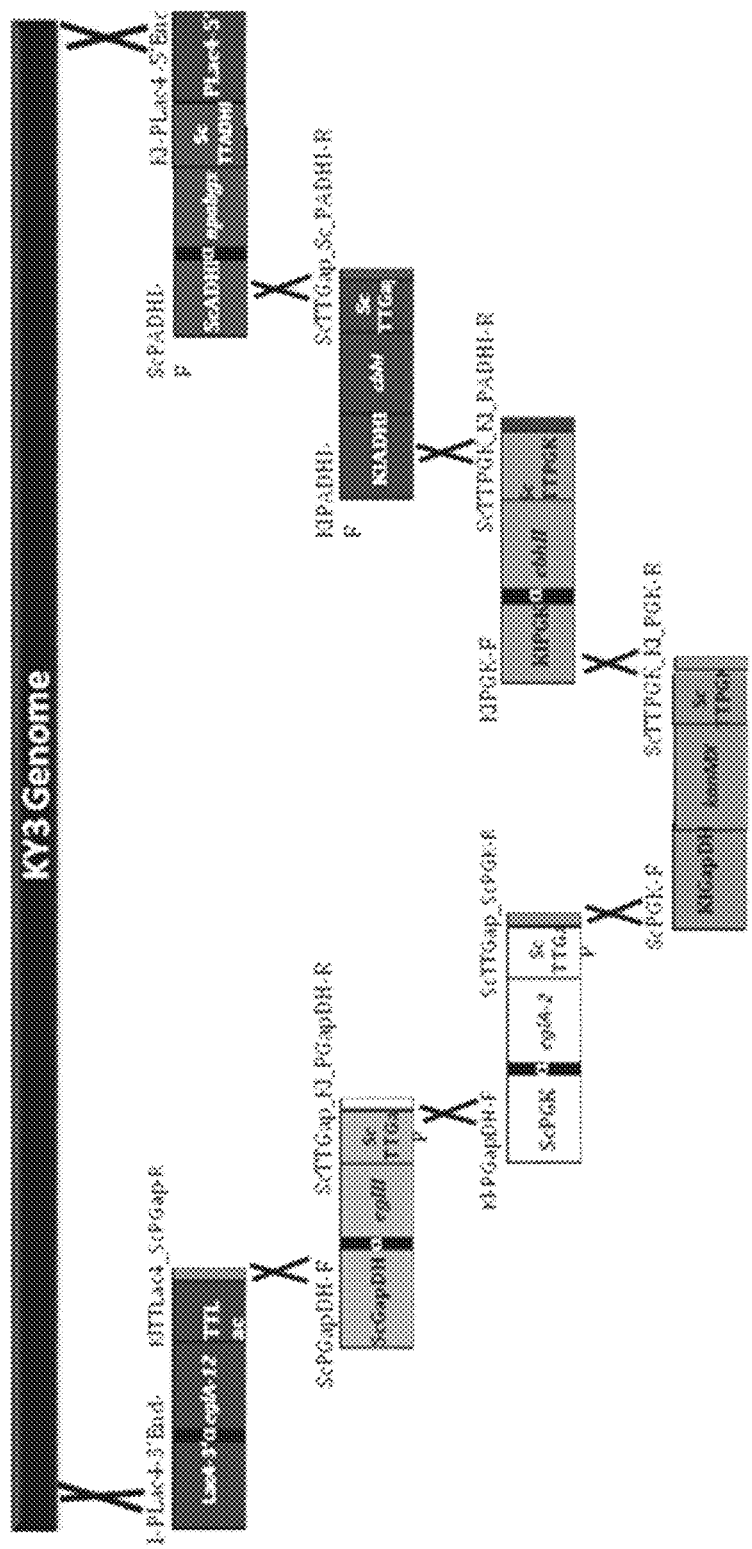
FIG. 5 is a schematic diagram showing exemplary gene cassettes and the genomic integration of 7 gene cassettes in strain KR7+.

The PGASO method was used to assemble into KY3 in a predetermined order six cellulase genes, i.e., cbhIII from *T. reesei* (encoding a 1,4-beta-D-glucan), cbhI from *T. reesei*, egIII from *T. reesei*, eglA-2 from *A. niger* (encoding an endoglucanase), eglA-12 (encoding an endoglucanase) from *A. niger*, and npabgs from *N. patriciarum*, plus a selection marker gene, kanMX. The seven gene cassettes, with a total length of ~2 Kb, were constructed in the predesignated order of eglA-12, egIII, eglA-2, kanMX, cbhII, cbhI, and npabgs; the promoter driving the genes were KlLac4, ScGapDH, ScPGK, KlGapDH, KlPGK, KlADHI, and ScADHI, respectively. See FIG. 5. The resultant strain was named KR7⁺.

The brown-rot fungus *T. reesei* simultaneously expresses three kinds of endo-β-1,4-glucanases. The major one is endoglucanase III (EGIII) when treated with a barley straw substrate. The gene product of egIII (Accession No. M19373.1), with 418 amino acids, contains a CBM 1 (cellulose binding domain) and a GH5 catalytic domain. *A. niger* can secrete two types of endoglucanase A (Egl A), i.e., EglA-2 and EglA-12, belonging to the GH2 family and the GH12 family, respectively. The gene product of eglA-2 (Accession No. XM_001397945.2), with 517 amino acids, also contains a CBM-1 and a GH2 catalytic domain. The gene product of eglA-12 (Accession No. GU724764.1) has only 239 amino acids and contains a GH12 catalytic domain.

Compared to another strain, the KR7 strain, the CBHI gene in KR7⁺ was linked to a stronger promoter, KlADHI, instead of the lowest strength promoter, KlGapDH, to increase the cellobiohydrolase productivity in KR7⁺. In addition, in KR7, the selection marker gene was driven by the strongest promoter, KlLac4, and was located at one terminus of the seven gene cassettes.

Figure 6:
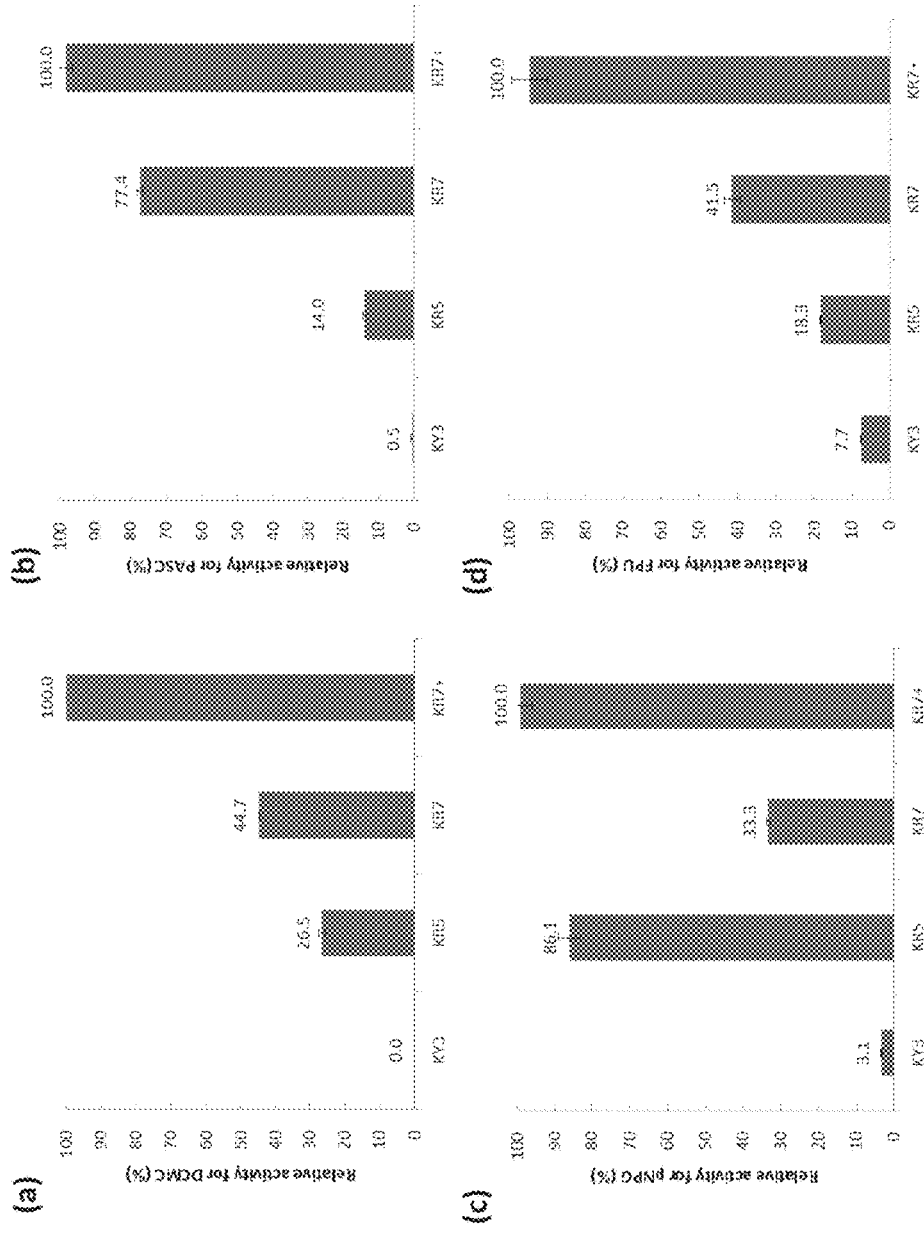
FIG. 6 is a set of bar graphs showing the cellulolytic enzyme activities in the supernatant of KR7+ culture.

In constructing KR7, a low transformation accuracy of the gene cassettes was observed. As compared to KR7, the transformation accuracy in constructing KR7+ was increased 2.6 folds, and an average of 8% colonies were found to have the correct assembly of the cassettes in the predesigned order. These observations suggest that the promoter strength and the location of the selection marker gene can be two important factors in the formulation of a cellulase cocktail. To quantify the activities of secreted cellulases, the supernatants of KY3, KR5, KR7 and KR7+ cultures were harvested and concentrated for analysis at 40° C. Data from relative activity assay with Dye-CMC as the substrate showed that the endo-β-1,4-glucanase activity in the supernatant of KR7+ was 2.3 times higher than that of KR7, probably due to the additional EglA-12 gene. See, FIG. 6, (a). The relative activity with PASC showed that the supernatant of KR7+ had a 1.2-fold improvement over KR7, probably due to the slight increase in the expression level of CBHI in KR7+. See, FIG. 6, (b). The relative activity of beta-glucosidase in the supernatant of KR7 was decreased, but the supernatant of KR7+ displayed a higher beta-glucosidase activity than those of KR5 and KR7. See, FIG. 6, (c). The overall cellulase activity assay was conducted using the filter paper assay (FPA), and the supernatant of KR7+ showed a 2.4-fold and a 5.5-fold improvement in the FPA activity over those of KR7 and KR5, respectively. See, FIG. 6, (d).

Figure 7:
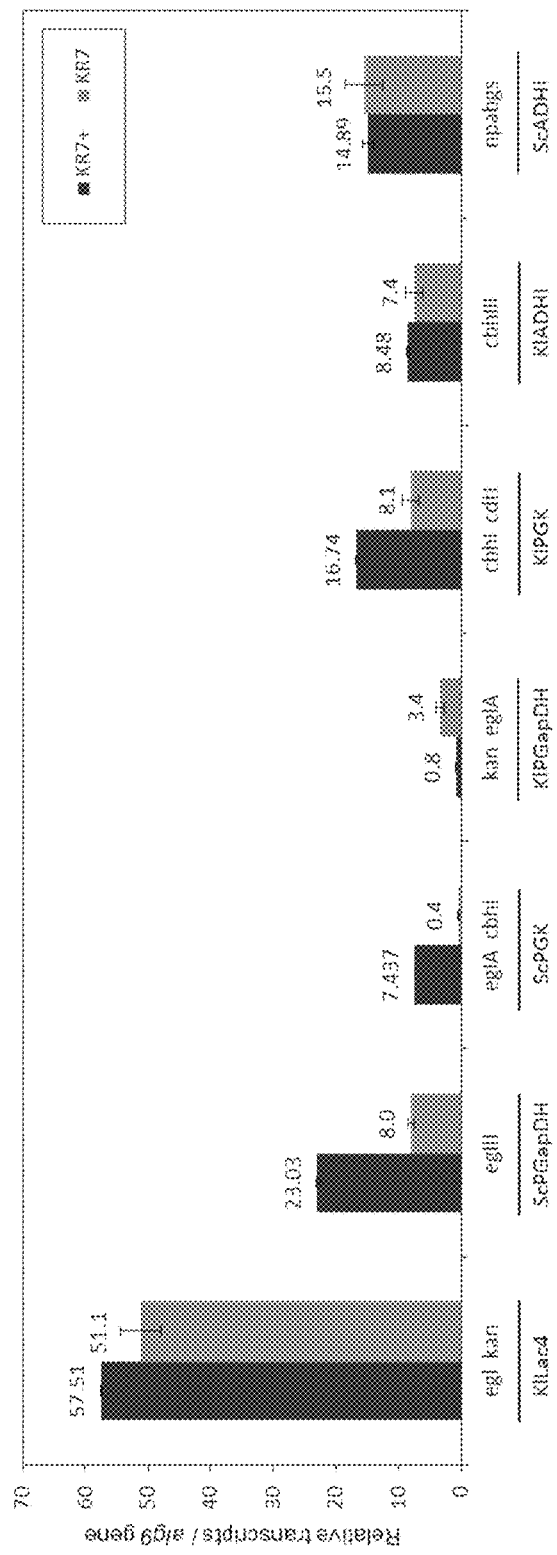
FIG. 7 is a graph showing transcription levels of genes in the KR7 and KR7+ strains by RT-PCR.

For monitoring the multiple gene co-expression, total RNA was also isolated from KR7+ that was grown at 30° C. in YPG medium for quantitative PCR analysis, and alg9 was employed as the reference gene. The mRNA levels of the seven genes of KR7+ were 57.51 (egI):23.03 (egIII):7.437 (eglA):0.8 (kanMX):16.74 (cbhI):8.48 (cbhII):14.89 (npabgs) relative to the indigenous alg9 gene. See, FIG. 7. Compared with the mRNA level of KR7 [51.1 (kanMX):8.0 (egIII):0.4 (cbhI):3.4 (eglA):8.1 (cbhII):7.4 (cdtI-gfp):15.5 (npabgs)], the result showed that the gene expression levels of the endoglucanase (eglA) and cellobiohydrolase (cbhI), which were driven by the KlGapDH and ScPGK promoters, were increased and the expression level of the selection marker gene reduced.

These data showed that the new strain, KR7+, was capable of co-expressing 6 different cellulases, and the secretion of their gene products displayed a synergistic effect on cellulolytic enzyme activities. It also showed that a desired co-expression profile can be achieved by promoter rearrangement and gene cassette replacement strategies in a yeast host.

EXAMPLE 3

Insertion of Seven Gene Cassettes

Figure 8:
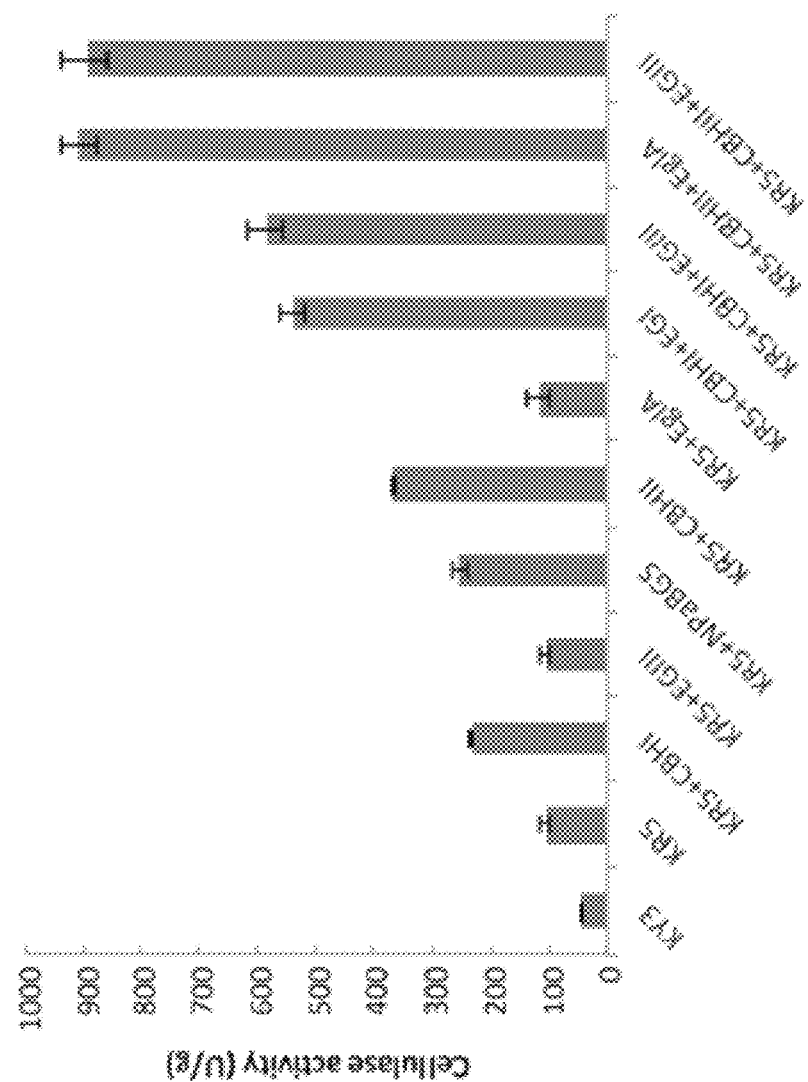
FIG. 8 is a bar graph showing synergistic effects of various enzymes with the crude enzymes of KR5 by a filter paper activity (FPA) assay.

In Example 1, we had engineered a recombinant *K. marxianus* strain, called KR5, that possesses the cbhI, egIII, and npabgs genes and can secrete the exoglucanase, endoglucanase, and beta-glucosidase enzymes simultaneously. Although KR5 could grow on media with cellodextrins, such as cellobiose and beta-glycan, it does not have the ability to utilize more complex cellulose substrates, such as filter paper and avicel. To improve the enzyme activity of KR5, we developed an enzyme cocktail strategy to investigate the synergistic actions with the crude enzymes of KR5. Many different glycosyl hydrolase (GH) family cellulases, including endoglucanase (EglA and EGIII), exoglucanase (CBHI and CBHII) and beta-glucosidase (purified NpaBGS), were used for cocktails with the supernatants of KR5 by mixing equal proportions of volume individually. One unit of FPA (filter paper assay) is defined as one μmol reducing sugar released from filter paper in one minute. As FPA is a widely accepted assay for the overall cellulase activity, we conducted an in vitro FPA assay, using the supernatant of the KR5 culture as the source of crude enzymes. The FPA data indicated only a 110 U/g overall cellulase activity in KR5. See FIG. 8.

Figure 9:
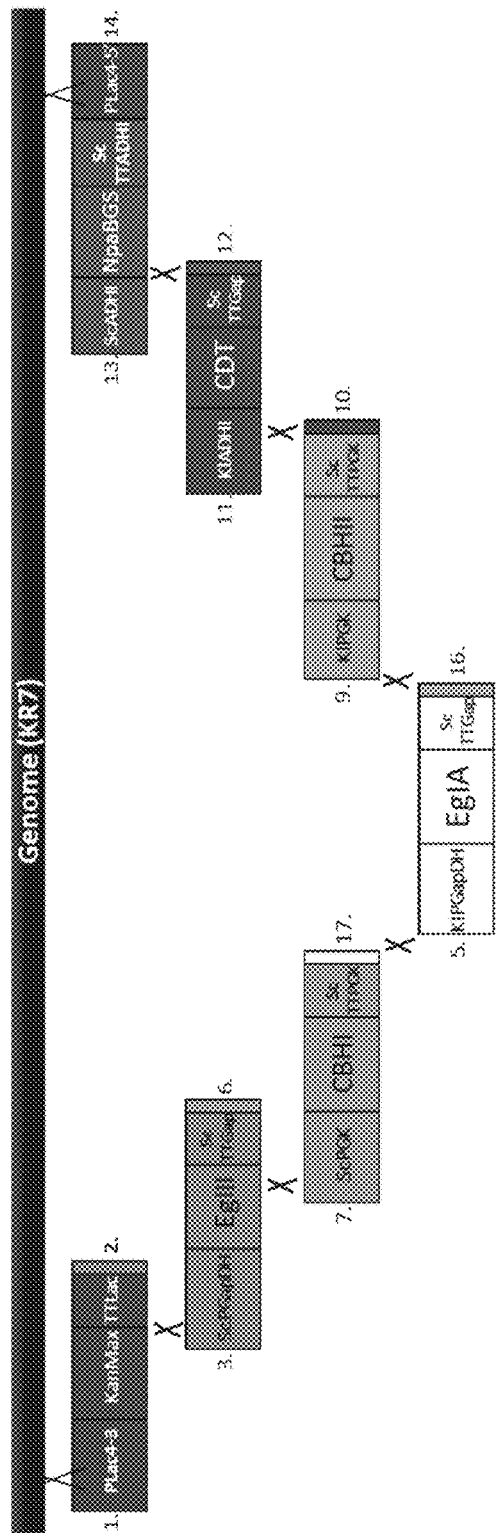
FIG. 9 is a schematic diagram showing exemplary gene cassettes and the genomic integration of 7 gene cassettes in strain KR7.
Figure 10:
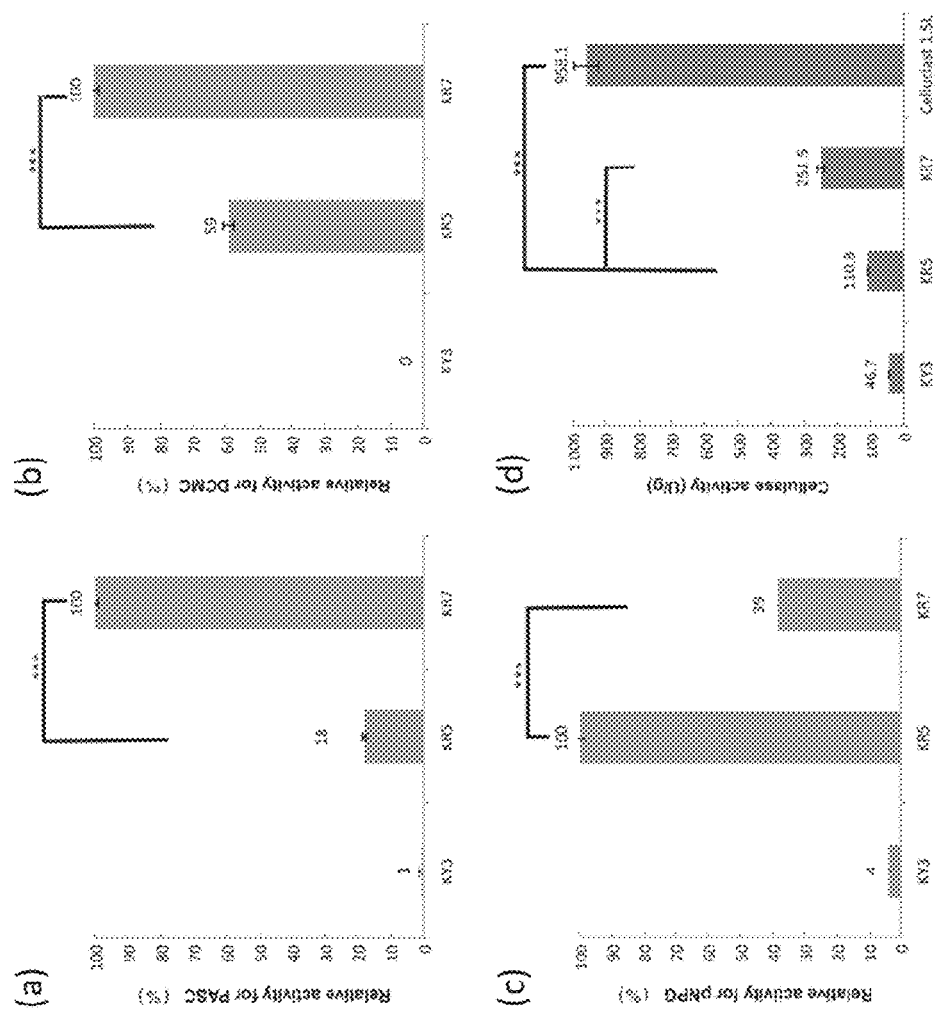
FIG. 10 is a set of bar graphs showing activities of the enzyme cocktail of the KR7 strain. (a) Endo-glucanase activity. (b) Exo-cellobiohydroxylase activity. (c) Cellulase activity. (d) Relative FPAs in different engineered strains.

According the data of the in vitro FPA assay, the above six genes plus a selection marker gene were one-step assembled into the WT genome with the order (KlLac4-kanMX, ScGapDH-egIII, ScPGK-cbhI, KlGapDH-eglA, KlPGK-cbhII, KlADHI-CDT, and ScADHI-npabgs) using PGASO. See FIG. 9. To quantify the activities of secreted cellulases, the supernatants of WT, KR5 and KR7 cultures were harvested and concentrated for analysis at 40° C. The relative activity assay with Dye-CMC as the substrate suggested that the EG activity in the supernatant of KR7 was 1.68 folds higher than that of KR5, probably due to secretion of the extra EglA (FIG. 10, *a*). The exoglucanase relative activity assay was performed with PASC (phosphoric acid-swollen cellulose) as the substrate, and the results indicated that the supernatant of KR7 had a 5-fold improvement over KR5, probably due to the presence of the extra CBHII in KR7 (FIG. 10, *c*). The relative activity assay with pNPG as the substrate showed that the beta-glucosidase activity in the supernatant of KR7 was not improved, being 2.5-fold lower than KR5 (FIG. 10, *b*). The overall cellulase activity assay was performed using the filter paper as the substrate, and the supernatant of KR7 culture showed a 2.27-fold improvement in the cellulase activity over KR5 (FIG. 10, *d*). These data demonstrated the simultaneous introduction of five fungal cellulase genes into the WT host, and their gene products were secreted with cellulolytic enzyme activities. Seven heterologous genes, including five cellulose genes, a cellodextrin transporter gene (CDT-1) from *Neurospora crassa* and a selection marker, were simultaneously transformed into the WT genome to derive a new strain, KR7, which could directly convert cellulose to ethanol.

EXAMPLE 4

A Strain with Nine Gene Cassettes Including Two Cellulase Booster Genes for Increasing the Cellulolytic Enzyme Efficiency In the SSF (simultaneous saccharification and fermentation) process for cellulosic ethanol production, the cellulolytic efficiency for sugar release should be faster than the sugar consuming for fermentation. Here, we demonstrated an enzyme synergistic optimization approach that overcame the cellulolytic rate limiting step in KR7+.

Figure 11:
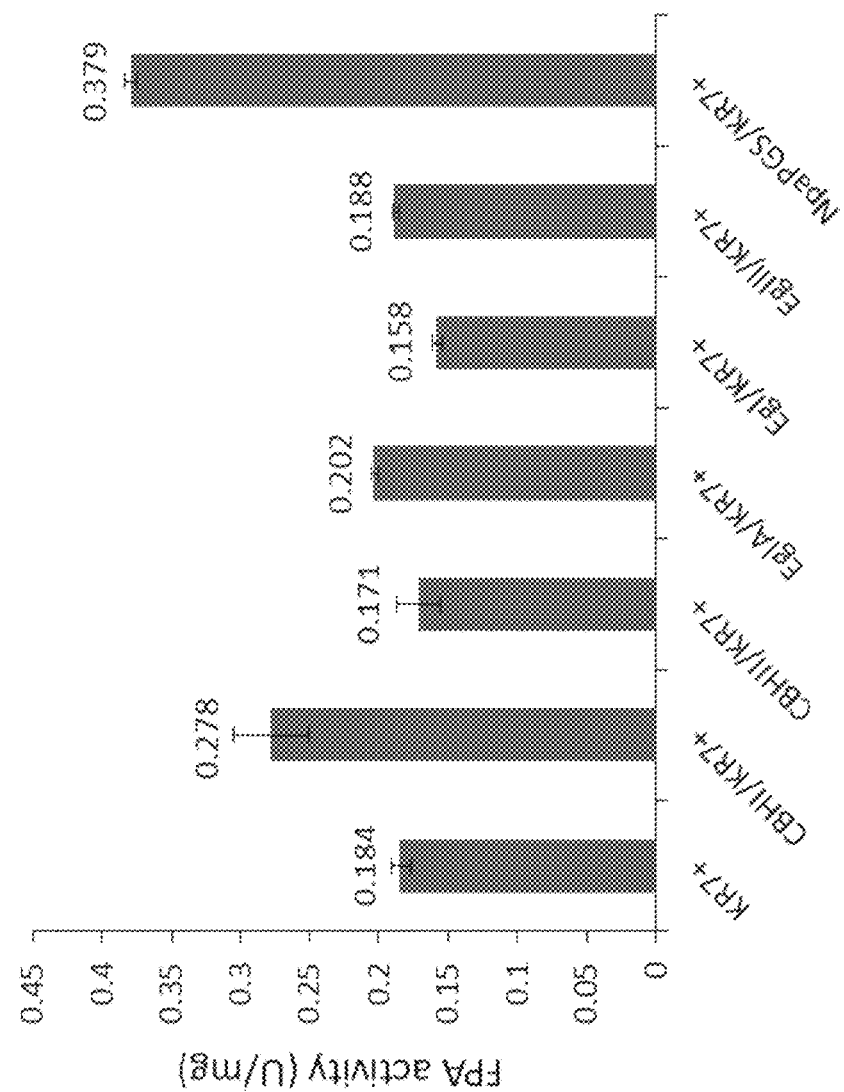
FIG. 11 is a bar graph showing synergistic effects of various enzymes with the crude enzymes of KR7+ by a FPA assay.

To optimize the cellulase expression, we conducted an FPA (filter paper activity) assay, which is widely accepted for determining the overall cellulase activity, to determinate the cellulolytic rate limiting step of the KR7+ strain. The supernatant of the KR7+ culture was used as the source of crude enzymes, and the FPA data indicated only a 0.184 U/mg overall cellulase activity. Then, we employed an enzyme cocktail strategy to investigate the synergistic actions with the crude enzymes of KR7+. The six different GH family cellulose genes, including egI, egIII, eglA, cbhII, cbhI, and npabgs, were individually introduced into WT and driven by the lac4 promoter for cellulase secretion. These supernatants of the engineered strains were added to the cocktail with the crude enzymes of KR7+ by mixing equal volumes. The enzyme cocktail results showed that increasing the amounts of CBHI (0.278 U/mg) or NpaBGS (0.379 U/mg) could significantly improve the total cellulolytic ability of KR7+ (FIG. 11).

Figure 12:
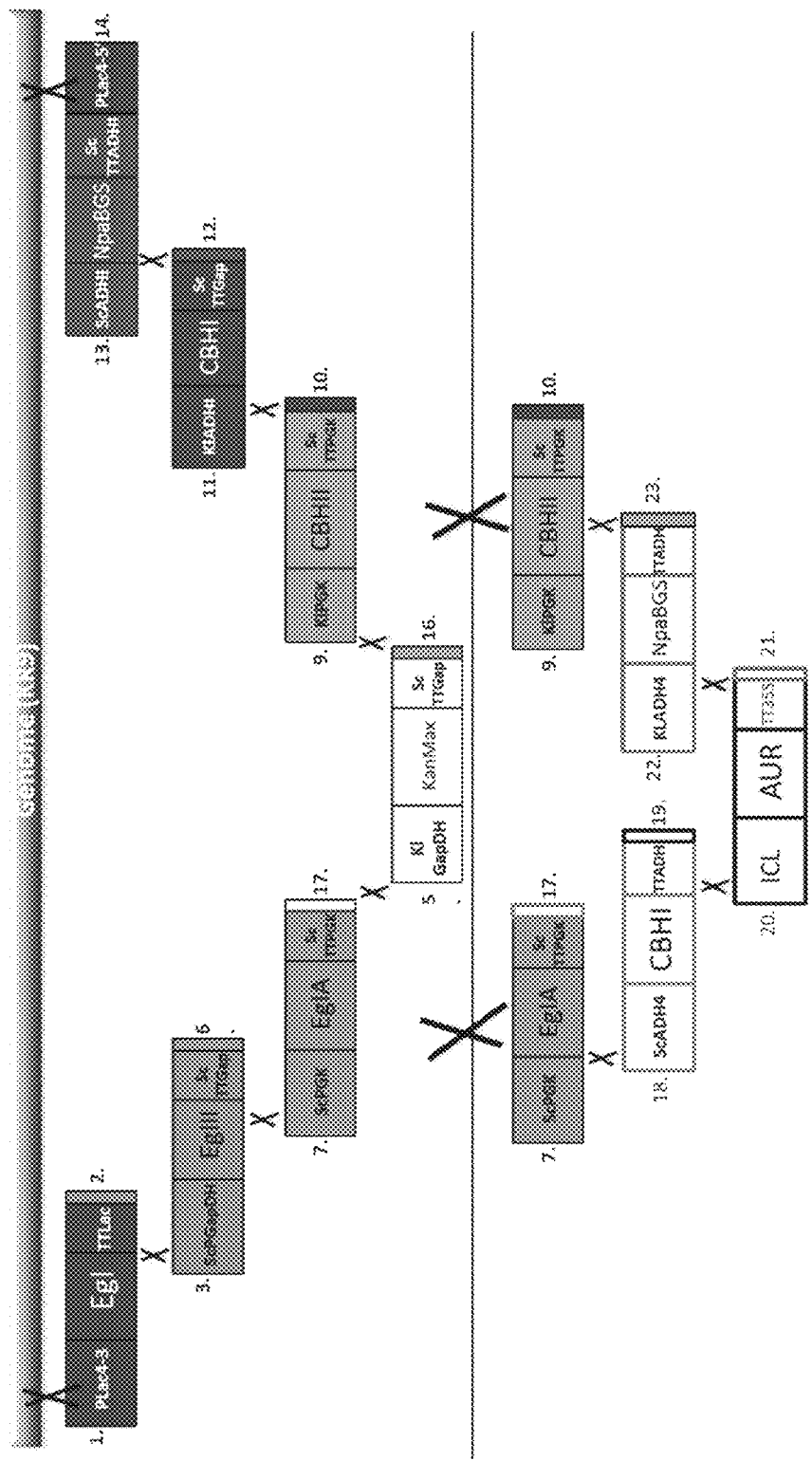
FIG. 12 is a schematic diagram showing the gene cassettes in the KR9 strain.
Figure 13:
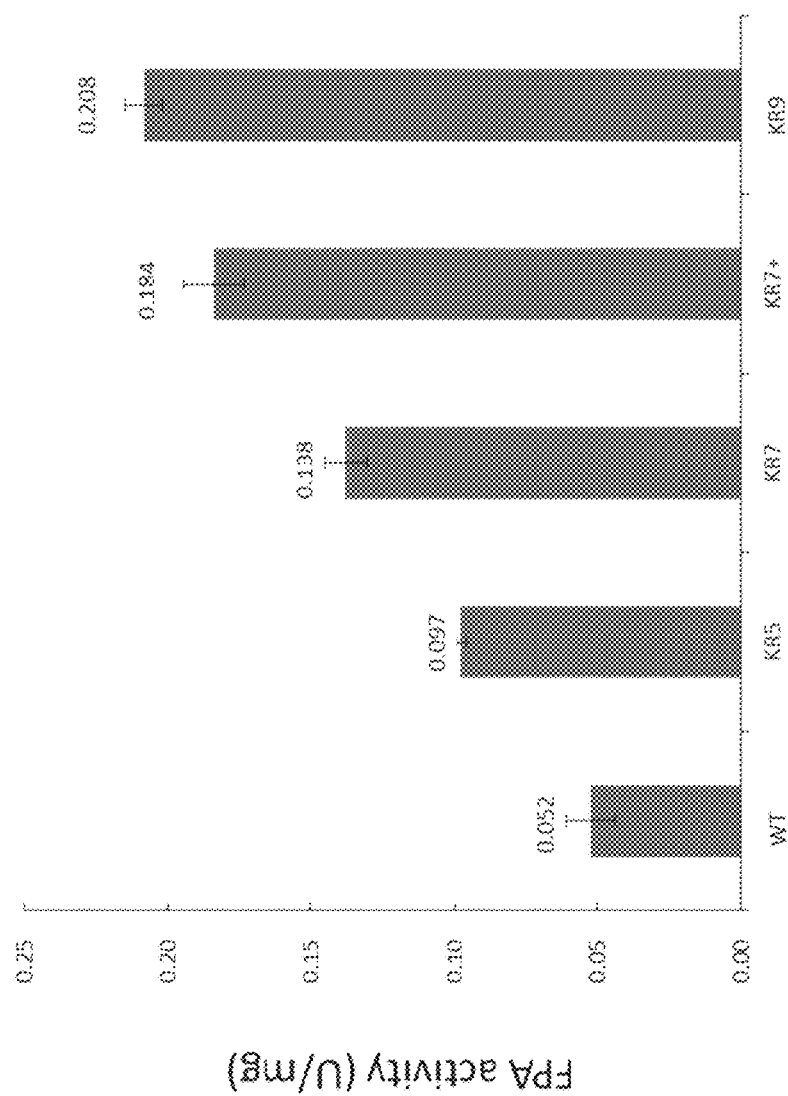
FIG. 13 is a bar graph comparing FPA activities of different engineered strains.

To increase the cellulase activity, the extra gene cassettes of cbhI and npabgs, which were driven by ScADH4 and KlADH4 promoters, were introduced into KR7+. The gene cassettes of ScPGK-eglA and KlPGK-cbhII were used as the homologous recombination regions and the ScPGK-aur gene cassette, expressing the selective marker aur, was used to replace the selective marker kanMX, generating the KR9 strain as shown in FIG. 12. In addition, the supernatant of KR9 cultures with a cocktail of cellulases showed a higher cellulolytic efficiency (0.208 U/mg) than KR7+ (0.184 U/mg), KR7 (0.138 U/mg), KR5 (0.097 U/mg), and WT (0.052 U/mg) in the FPA assay (FIG. 13).

Figure 14:
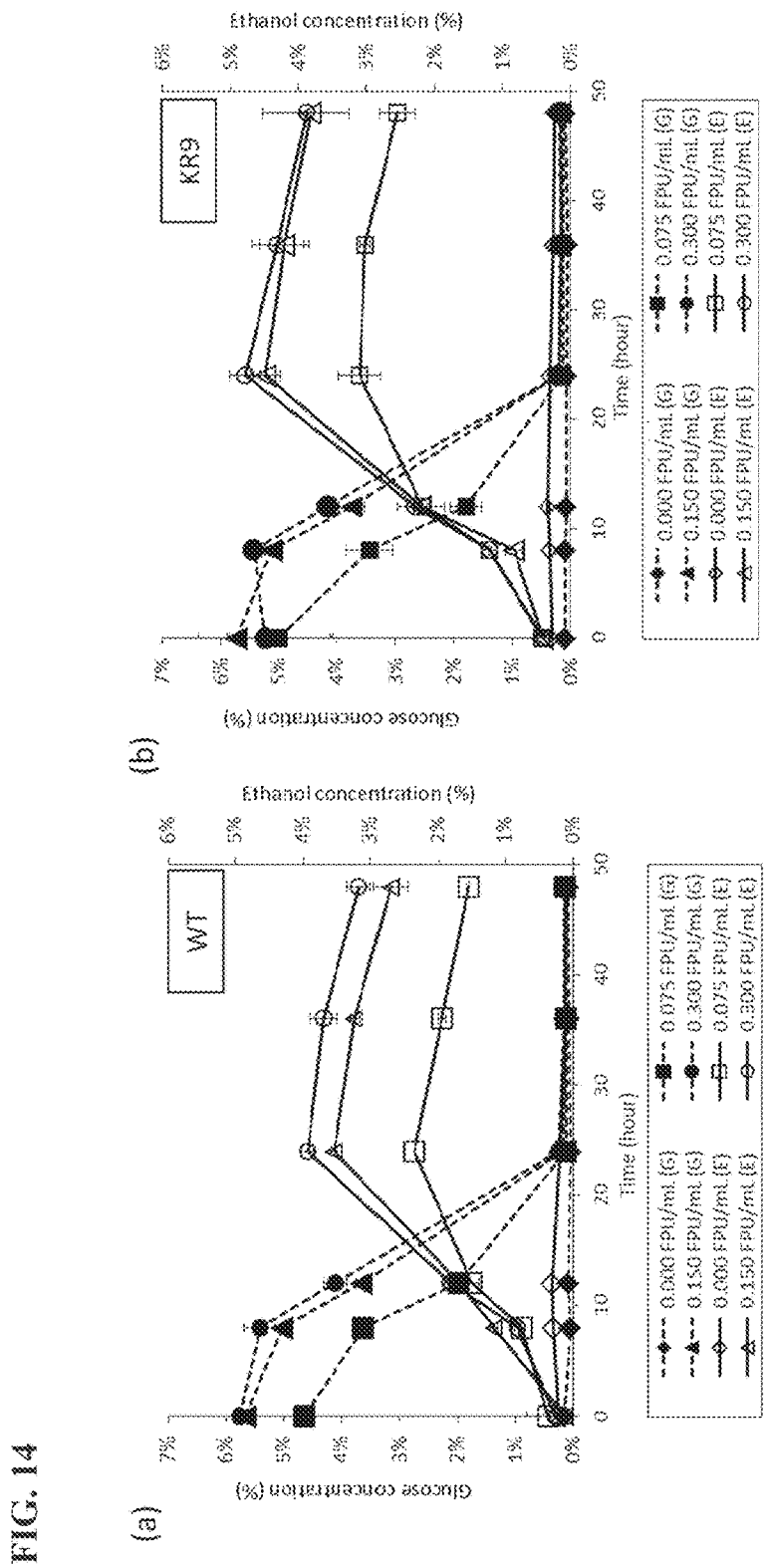
FIG. 14 is a set of graphs showing glucose consumption and ethanol productivity of the (a) WT and (b) KY9.

To demonstrate the SSF capability of these engineered strains, pretreated rice straw was used as the substrate to verify the cellulose utilization and ethanol fermentation. The pretreated rice straw was further processed by the enzyme scarification with different concentration of celluclast 1.5 L at 50° C. for 72 hours, and the pre-culturing yeast cells of WT and KR9 were inoculated for the fermentation test. The ethanol conversion was assayed by HPLC, and the results indicated that increasing the enzyme concentration increased glucose release from the pretreated rice straw samples, and also increased the ethanol production in both yeast strains (FIG. 14). The data showed that KR9 could convert the ethanol more efficiently than WT in three aspects. First, a higher production of ethanol could be achieved by KR9 than by WT (4% vs. 3% for 30 min) (FIG. 14, $a$ and $b$). Second, as compared to WT, KR9 could shorten the enzymatic reaction time to produce the same amount of ethanol; for example, it could produce 3% ethanol within 20 hours (FIG. 14, $b$), while WT took more than 24 hours (FIG. 14, $a$). Third, KR9 used less enzyme (0.15 FPU/mL) to produce more ethanol (4%) (FIG. 14, $b$) compared with WT (0.3 FPU/mL enzyme for 3% ethanol) (FIG. 14, $a$). It appears that KR9 not only possesses an improved cellulosic ethanol conversion ability, but also can reduce the enzyme cost in the SSF process.

Figure 15:
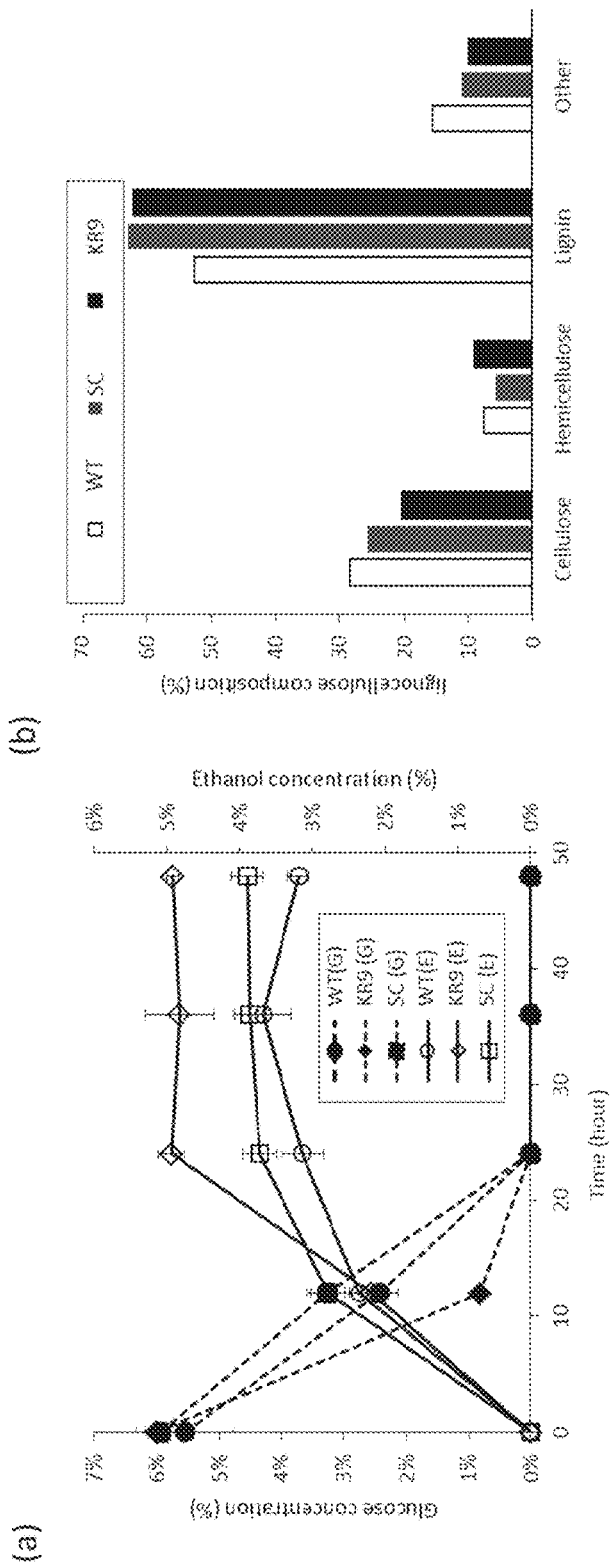
FIG. 15 is a set of graphs showing activities of engineered *K. marxianus* strains and a commercial strain (SC). (a) Glucose consumption and ethanol productivity. (b) simultaneous saccharification and fermentation (SSF) assay.

To compare with a current industrial process, a commercial *S. cerevisiae* (SC) strain was employed for the SSF test. Rice straw samples pretreated with enzymatic scarification by 0.15 FPU/mL celluclast 1.5 L was used as the substrate to estimate the bio-conversion rate. KR9 was capable of producing a higher ethanol concentration (5%) than WT (3%) and SC (4%) after SSF. See, FIG. 15, $a$. These data indicated that the cellulosic ethanol conversion ability of KR9 was not only 1.25-fold higher than the strain SC, but also 1.67-fold faster. After the fermentation test, a cellulose composition assay was done with insoluble rice straw samples. KR9 showed a more efficient ability to decompose cellulose and other sources, i.e., about 20% and 10% higher than WT and SC, respectively (FIG. 15, $b$).

The data demonstrated that the engineered strain can improve the cellulose utilization in the SSF process.

EXAMPLE 5

A Strain with Nine Gene Cassettes Including Two Cellulase Booster Genes for Increasing the Cellulolytic Enzyme Efficiency In this example, the cellulolytic enzyme efficiency was increased by integrating two peripheral enzymes as the cellulose booster. Apart from the traditional hydrolytic cellulase enzymes, a new class of oxidative enzymes, called lytic polysaccharide monooxygenases (LPMO, lpmo), can effectively degrade the crystalline cellulose and enhance the hydrolytic activity of other cellulase enzymes. Hence, LPMO has been named as a "cellulase booster" and classified as belonging to auxiliary activity family 9 (AA9). This copper containing LPMO requires an electron for its activity, which may be provided by enzymatic donor, i.e., cellobiose dehydrogenase (CDH, cdhI) or non-enzymatic donor, i.e., ascorbate. Hence we improved the cellulolytic efficiency of KR7+ by integrating the cellulase booster LPMO and its enzyme partner CDH. The genes encoding for LPMO and CDH were selected from *Thermoascus aurantiacus* and *Myceliophthora thermophila*, respectively. Both genes were codon optimized for *K. marxianus* and synthesized commercially by GeneScript Inc (Piscataway, N.J., USA). For chromosomal integration and subsequent identification, these genes were separately cloned into pKlac2-α-12His vector, which fuses a 12 His tag into the C-terminal of both enzymes. The equimolar ratios of SacII digested gene cassettes of lpmo and cdhI were integrated into the Lac4 region of KR7+ and the wild type control (WT). This new strain is called KR7++LC.

Figure 16:
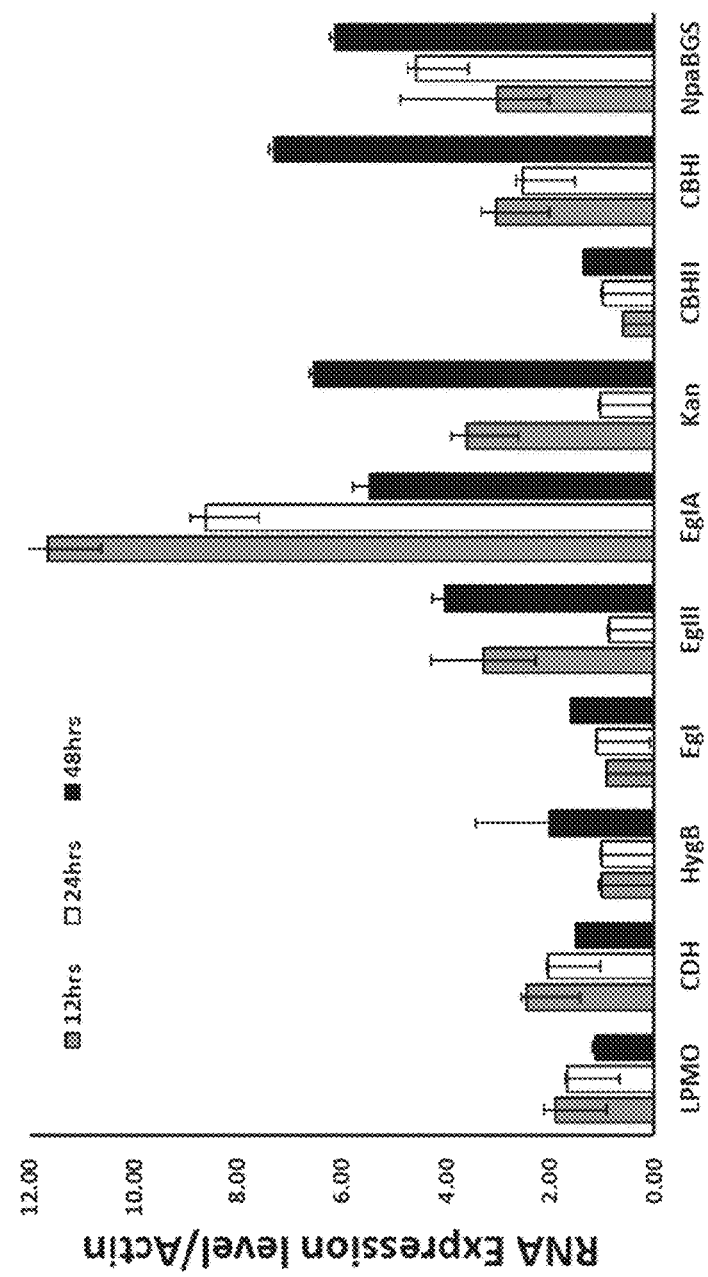
FIG. 16 is a graph showing transcription levels of genes in KR9++LC by RT-PCR.

To confirm the expression of integrated genes, total RNA was isolated from KR7++LC at different time intervals and qPCR was performed subsequently. The expression level of each gene was calculated based on the relative expression of β-actin gene and the data revealed that all of the inserted genes were expressed. This result suggested that the random insertion of lpmo and cdhI did not affect the previously integrated cellulase genes (FIG. 16). Western blot analysis of culture supernatant using anti-His antibody confirmed the expression of both enzymes.

Figure 17:
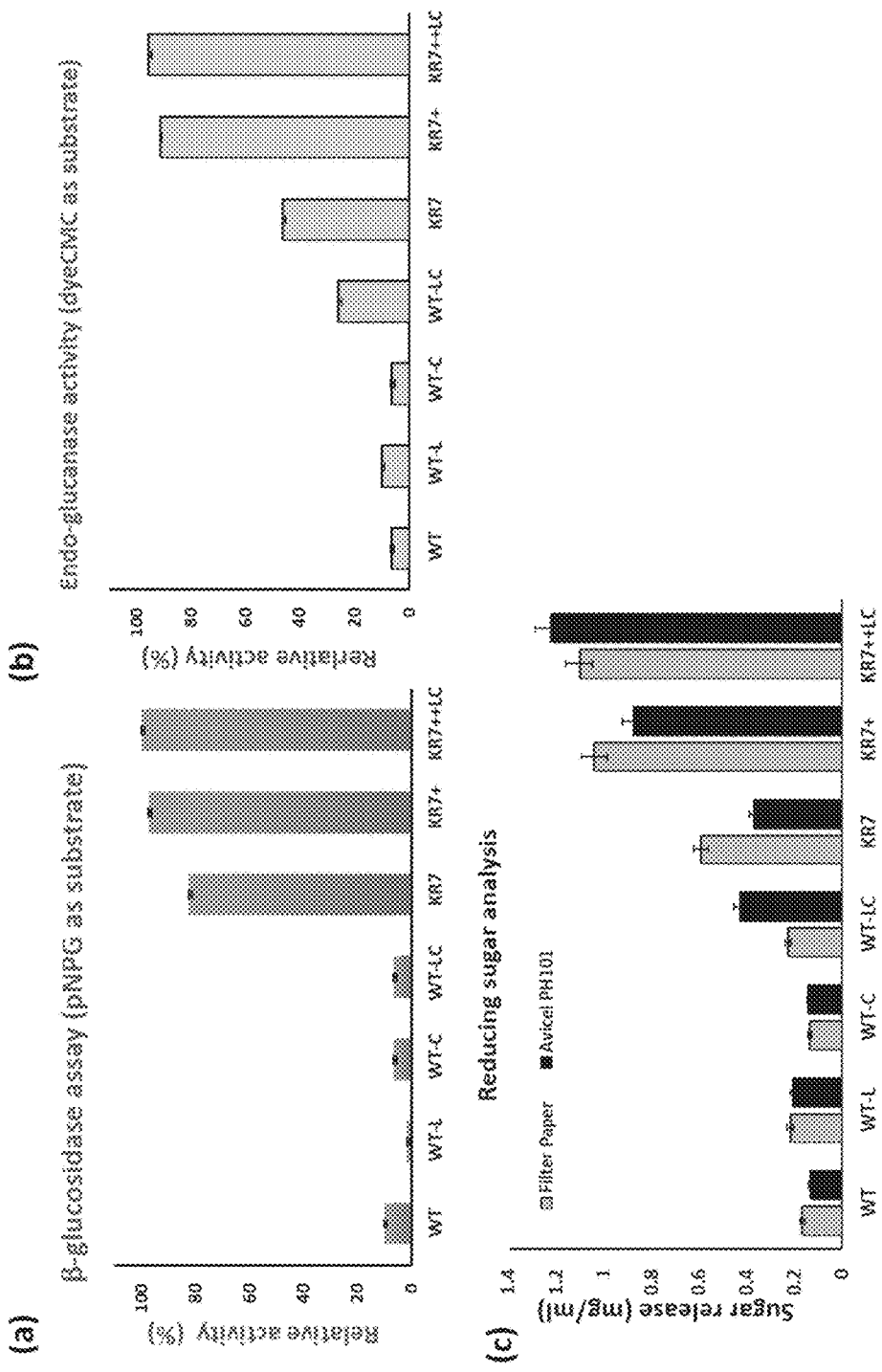
FIG. 17 is a set of graphs showing activities of the KR9++LC strain. (a) Beta-glucosidase activity. (b) Endo-glucanase activity. (c) FPA activity and Avicel assay.

Beta-glucosidase and endoglucanase assays were conducted to confirm whether the integration of lpmo and cdhI can increase activity. The enzyme activity of KR7+-FLC remained the same as in the wild type counterpart (FIG. 17, $a,b$). We conducted a soluble sugar release analysis using filter paper as the substrate and found that KR7++LC increased the total sugar release compared with KR7+ and KR9 (FIG. 17, $c$). To evaluate the effect of LPMO on crystalline cellulose we incubated the enzymes with Avicel PH101. The KR7++LC showed 0.5 fold increase in the overall sugar release compared with KR7+. Similarly, the wild type with LPMO and CDH (WT-LC) significantly boosted the sugar release (FIG. 17, $c$). Thus, KR7++LC could improve the sugar release from the crystallized cellulose Avicel. These data indicate that the cellulase booster can significantly improve the cellulolytic activity of the designer strain.

EXAMPLE 6

Materials and Methods (1) Strain Construction

To construct the engineered strains described in the examples above, we used the PGASO transformation technique. The cells were spread onto YPG plates (1% BactoDifco-Yeast Extract, 2% BactoDifco-Peptone, and 2% Merck-galactose) containing G418 (200 μg/mL, InvivoGen, USA). The engineered yeast KR7+ and KR9 were obtained via application of PGASO to assemble seven gene cassettes in a predesignated order. Consecutive gene cassettes containing overlapping 55 bp regions on the borders were used for recombining the cassettes from the first to the seventh. In the fifth gene cassette, the kanMX gene and the KlGapDH promoter sequence were amplified and assembled into a fragment to be employed as the selection marker for the strain construction. Furthermore, the aur gene was amplified to serve as selection marker in the KR9 strain construction via selection marker recycling. The primer pairs used in this study are listed in Table 4. The numbers shown in FIG. 12 correspond to the numbers in the primer names To verify the assembled order of the gene cassettes, each isolated colony was digested in QucikExtract™ DNA Extraction Solution (EPICENTRE, Madison, Wis.) to remove yeast cell wall and was then examined by PCR with gene specific checking primers. See Table 4. The uniqueness of the first 55 bp of each promoter was confirmed by using the sequence as the query sequence in the Blast search against the genomes of S. cerevisiae and K. lactis (nucleotide blast program in NCBI) by selecting "more dissimilar sequences" and also against our genome draft of K. marxianus with the default parameter setting.

(2) RT-qPCR Quantification

The engineered strains were incubated in 5 mL YPG medium at 30° C. with shaking at 200 rpm for 16 hr. The genomic DNA was purified from yeast cells using HiQ-Column 12 automated DNA/RNA Purification System (Protech, Taiwan) with an AccuPure Yeast DNA mini kit (AccuBioMed, Taiwan). The template RNA was purified from yeast cells using HiQ-Column 12 automated DNA/RNA Purification System (Protech, Taiwan) with an AccuPure Yeast RNA mini kit (AccuBioMed, Taiwan). cDNA synthesis was conducted using a reverse transcription kit (SuperScript™ II kit, Invitrogen). The relative quantification of each gene was carried out via the Universal Probe Library Set (LightCycler® 480 Probes Master, Roche) on a LightCycler (LightCycler 480, Roche), following the protocol of the manufacturer, and the designer UPL primer sets were used to analyze the driven strength of each promoters (Table

TABLE 4

| Primer | Sequence (5' to 3') |
|---|---|
| Kit1-1F | CCGCGGGGATCGACTCATAAAATAG (SEQ ID NO: 41) |
| Kit1-2R | CTACTATTAATTATTTACGTATTCTTTGAAATGGCAGTATTGATAATGATAAACTTATACAACATCGAAGAAGAGTCT (SEQ ID NO: 42) |
| Kitt-3F | AGTTTATCATTATCAATACTGCCAT (SEQ ID NO: 43) |
| Kit2-6R | AATCGATTTACAGAAACTTGCACACTAAAAATACACAACTAAAAGCAATTACAGTTGGCGGAAAAAATTCATTTGTAA (SEQ ID NO: 44) |
| Kit3-7F | ACTGTAATTGCTTTTAGTTGTGTAT (SEQ ID NO: 45) |
| Kit3-17R | GCGTCTATGTTGGAATTTGACCCCAAAAACCATCAATTCCTTCGTTCTAAGCCCCAAGCTTTTTCGAAACGCAGAA (SEQ ID NO: 46) |
| Kit4-5F | AGTATGGTAACGACCGTACAGGCAA (SEQ ID NO: 47) |
| Kit4-16R | CATATACCTTTGATACCATAAAAACAAGCAAATATTCTTACTTCAAACACACCCGTGGCGGAAAAAATTCATTTGTAA (SEQ ID NO: 48) |
| Kit5-9F | CGGGTGTGTTTGAAGTAAGAATATT (SEQ ID NO: 49) |
| Kit5-10R | AGGTAAGTATGGTAACGACCGTACAGGCAAGCGCGAAGGCAAATGGAAAAGCTGGAAGCTTTTTCGAAACGCAGAATTTT (SEQ ID NO: 50) |
| Kith-11F | CCAGCTTTTCCATTTGCCTTCGCGCTTGCC (SEQ ID NO: 51) |
| Kith-12R | GGAATCCCGATGTATGGGTTTGGTTGCCAGAAAAGAGGAAGTCCATATTGTACACTGGCGGAAAAAATTCATTTGTAA (SEQ ID NO: 52) |
| Kit7-13F | GTGTACAATATGGACTTCCTCTTTTC (SEQ ID NO: 53) |
| Kit7-14R | GAAATTTAGGAATTTTAAACTTG (SEQ ID NO: 54) |
| Kit8-18F | GGGGCTTAGAACGAAGGAATTG (SEQ ID NO: 55) |
| Kit8-19R | AATATTCCCTTGATGATATCCAACTGTTGGTTCTTGATTTCTTCAGACGGATCTCGAATAAAAAAATATGCGCATGTGAA (SEQ ID NO: 56) |
| Kit9-20F | GAGATCCGTCTGAAGAAATCAAGAA (SEQ ID NO: 57) |
| Kit9-21R | CCAAAACAATCAATTTCTGGGTGTTGAACTTCTATTAGTAGCCGTTGATAGATCTGGAGCTTCCAGGGGGAAACGC (SEQ ID NO: 58) |
| Kit10-22F | AGATCTATCAACGGCTACTAATAGAAGT (SEQ ID NO: 59) |
| Kit10-23R | CATATACCTTTGATACCATAAAAACAAGCAAATATTCTTACTTCAAACACACCCGTTAAAAAATACACATAAATTAATGCTAGT (SEQ ID NO: 60) |

5). Alg9 or the actin gene was used as a reference gene for quantitative PCR analysis, and each analysis was repeated three times.

TABLE 5

| Primer name | Sequence |
|---|---|
| Kan-UPL#144F | 5'-AGACTAAACTGGCTGACGGAAT-3' (SEQ ID NO: 61) |
| Kan-UPL#144R | 5'-CATCAGGAGTACGGATAAAATGC-3' (SEQ ID NO: 62) |
| EgIII-UPL#77F | 5'-TGGCTCCGACAGAACAATC-3' (SEQ ID NO: 63) |
| EgIII-UPL#77R | 5'-GTCTTGTATGCAGGACTGAACG-3' (SEQ ID NO: 64) |
| CBHI-UPL#77F | 5'-ACATCAAGTTCGGACCCATT-3' (SEQ ID NO: 65) |
| CBHI-UPL#77R | 5'-GGTAGGTCCGGGAGAGCTT-3' (SEQ ID NO: 66) |
| EgI-UPL #75 F | 5'-GGCGTCAACTCCGTGTGT-3' (SEQ ID NO: 67) |
| EgI-UPL #75 R | 5'-AGGAAGCACCAACCCAGAC-3' (SEQ ID NO: 68) |
| CbhII-UPL #60F | 5'-CGCTTCCGTTTACAAGAACG-3' (SEQ ID NO: 69) |
| CbhII-UPL #60R | 5'-AACGTTGGTAGCCAAACCTC-3' (SEQ ID NO: 70) |
| NpaBGS-UPL#150F | 5'-GAAGCTGTAATGGAAGAAGATGG-3' (SEQ ID NO: 71) |
| NpaBGS-UPL#150R | 5'-CTGGGAATGAAAGGAAAATCAT-3' (SEQ ID NO: 72) |
| ACTIN-UPL #9F | 5'-GCGTAGATTGGAACAACGTG-3' (SEQ ID NO: 73) |
| ACTIN-UPL #9R | 5'-AGAACTACCGGTATTGTGTTGGA-3' (SEQ ID NO: 74) |

(3) Enzyme Cocktail and Activity Assay

The supernatants collected from yeast cultures were prepared for cellulase activity assays. For the total cellulase assay, 0.8 mg/mL 4-methylumbelliferyl-β-D-cellobiopyranoside (MUC) was used for the glucanase activity assay at 30° C. for 1 hr. The enzyme activity of released 4-methylumbelliferone (MU) was measured by the fluorescent intensity reader (SpectraMax M2, MDS) with excitation and emission wavelengths at 365 nm and 465 nm.

0.4% (w/v) Azo-CM-Cellulose (Dye-CMC) (Megazyme, Wicklow, Ireland) was used in the relative activity of endoglucanase assay at 30° C. for 6 hours, and the detection was done by absorption of 590 nm.

For the exo-cellobiohydrolase assay, 0.4% (w/v) phosphoric acid-swollen cellulose (PASC) was used for the relative activity assay at 30° C. for 24 hrs. After the hydrolysis reaction, the amount of reducing sugar was measured using the Somogyi-Nelson method to determine the number of glucose equivalents.

The filter paper was used for the crude extra-cellular enzyme digestion at 40° C. for 8 hours (one unit of FPA is defined as 1 mmol reducing sugar released from filter paper in 1 minute). 60 FPU/mL Celluclast 1.5 L (Novozyme, Denmark) was used as the benchmark. The commercial enzyme and yeast produced enzymes were assayed at 30° C. with the same protein concentration (1.5 mg/mL). The protein concentration was determined by the Bradford method (Micro BCA™ Protein Assay Kit, Thermo Scientific, USA).

(4) Estimation of Carbon Utility and Ethanol Production

Transformed yeast cells were grown on 2% agar YP medium plates with pretreated rice straw, which was kindly provided from Far Eastern New Century Corporation, as the single carbon source. For the SSF test of the engineered yeasts, the pretreated rice straw samples were used for further enzymatic scarification by Celluclast 1.5 L (Novozymes, Copenhagen, Denmark) with different concentrations, including 0.3 FPU/mL, 0.15 FPU/mL, 0.075 FPU/mL and 0 FPU/mL. After 72 hours of the enzymatic scarification process at 50° C., the rice straw samples were inoculated with the engineered yeasts to be converted to ethanol at 37° C. This recipe in liquid medium was also used for yeast growth and ethanol fermentation. The semi-anaerobic batch culturing was conducted in a 250 mL serum bottle with 50 mL of medium with pretreated rice straw 10.0 g in the bottle at 37° C., 200 rpm rolling for 48 hours. The initial inoculated cell density for each sample had an O.D. of 20 at a wavelength of 600 nm using a spectrophotometer (Ultrospec 2100 pro, Amersham Bioscience, UK). Total glucose concentration and the productivity of ethanol were analyzed by HPLC (Jasco PU-2089 Quaternary HPLC PUMP, JASCO International Co., Ltd., Japan) with thICSep ICE-CORE-GEL 87H3 Column (Transgenomic, USA) and Shodex RI-101 Refractive Index Detector (ECOM, Czech Republic). Each fermentation experiment and the subsequent analysis were repeated three times.

(5) Lignocellulose Composition Assay

To analyze the cellulose, hemicellulose and lignin contents, the crude fiber content in biomass was determined using the method described by association of analytical communities AOAC (Official methods of analysis 2002:04, AOAC International, Gaithersburg, Md., USA.). After drying in an oven for about 1 hour at 105° C., the crucible was weighted and cooled in a desiccator. The 1.0 g samples and 1.0 g Celite 545 diatomaceous earth filtered agent (Sigma Aldrich, Germany) were dissolved in 200 mL 0.25 N boiling sulfuric acid and boiled for 30 min for fibertec analysis (Fibertec™ 2010, Foss Analytical, Denmark). The hydrolyzed mixture was filtered through the crucible and the residue was rinsed with boiled distilled water to remove the acid from the filtrate inside the crucible. 200 mL 0.313 N boiled sodium hydroxide (NaOH) liquid was added to the crucible and boiled for 30 min. The hydrolyzed samples were filtered again, and the residue was rinsed with boiled distilled water until the crucible was free of alkaline. The residue was rinsed again with a small amount of acetone and then drained. The residue in the crucible was dried in the oven at 105° C. until a constant weight was achieved. The crucible was placed in the muffle furnace at 550° C. to burn completely. After achieving a constant weight in the desiccator, the crucible was calculated as:

$$\text{(Weight of residue without ash)/(weight Sample)} \times 100\% = \% \text{ Crude Fiber}$$

The neutral detergent fiber (NDF) was determined using the method described by AOAC to obtain the total amount of cellulose, hemicellulose and lignin after the crude fiber content was estimated. Furthermore, an acid detergent solution was applied to treat the NDF to obtain the acid detergent fiber (ADF), which contains the cellulose and lignin. The ADF was treated by 73% $H_2SO_4$ solution again to obtain the lignin content named the acid detergent lignin (ADL). The cellulose, hemicellulose and lignin contents are shown as follows: Cellulose content (%)=ADF-ADL; Hemicellulose content (%)=NDF-ADF; Lignin content (%)=ADL

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An engineered *Kluyveromyces marxianus* cell, the cell comprising in its genome:
   (i) two different nucleic acid molecules that each contain a promoter operably linked to a gene encoding a functional enzyme, and
   (ii) a selection nucleic acid molecule that contains a promoter operably linked to a gene encoding a selectable marker, wherein all of the nucleic acids molecules of (i) and (ii) are in tandem, the engineered cell expresses all of the proteins encoded by the genes of (i) and (ii), and each functional enzyme is a cellulolytic enzyme.

2. The engineered cell of claim 1, further comprising:
   (iii) a reporter nucleic acid molecule that contains a promoter operably linked to a gene encoding a reporter, or
   (iv) a scaffold nucleic acid molecule that contains a promoter operably linked to a gene encoding a scaffold polypeptide, wherein all of the nucleic acids molecules of (i) and (ii), and (iii) or (iv) are in tandem and the engineered cell further expresses all of the proteins encoded by the genes of (iii) or (iv).

3. The engineered cell of claim 2, wherein each of the promoters of (i), (ii), (iii), and (iv) are selected from the group consisting of an *S. cerevisiae* GapDHI promoter, an *S. cerevisiae* AdhI promoter, an *S. cerevisiae* PGK promoter, an *S. cerevisiae* Adh4 promoter, an *S. cerevisiae* TDH3 promoter, an *S. cerevisiae* TEF1 promoter, an *S. cerevisiae* TPI1 promoter, an *S. cerevisiae* GAL1 promoter, an *S. cerevisiae* GAL7 promoter, an *S. cerevisiae* GAL10 promoter, an *S. cerevisiae* CUP1 promoter, an *S. cerevisiae* ICL1 promoter, a *K. lactis* GapDHI promoter, a *K. lactis*

PGK promoter, a *K. lactis* AdhI promoter, a *K. lactis* Lac4 promoter, a *K. lactis* Adh4 promoter, and a *C. tropicalis* ICL promoter.

4. The engineered cell of claim 1, wherein each gene of (i) is selected from the group consisting of a *T. reesei* egIII gene, a *T. reesei* cbhI gene, a *T. reesei* cbhII gene, a *N. patriciarum* npabgs gene, an *A. niger* eglA gene, an *A. niger* egI gene, a *N. crassa* cdt-1 gene, a *T. aurantiacus* lpmo gene, a *M. thermophila* cdhI gene, a *T. fusca* lpmo gene, a *C. thermocellum* celK gene, a *C. thermocellum* celS gene, a *C. thermocellum* celA gene, a *C. thermocellum* celR gene, and a *C. thermocellum* xynC gene.

5. The engineered cell of claim 1, wherein the promoter and the gene in each nucleic acid molecule of (i) are selected from the group consisting of:
   (a) an *S. cerevisiae* GapDHI promoter and a *T. reesei* egIII gene,
   (b) an *S. cerevisiae* AdhI promoter and a *N. patriciarum* npabgs gene,
   (c) an *S. cerevisiae* PGK promoter and a *T. reesei* cbhI gene,
   (d) an *S. cerevisiae* PGK promoter and an *A. niger* eglA gene,
   (e) an *S. cerevisiae* Adh4 promoter and a *T. reesei* cbhI gene,
   (f) a *K. lactis* GapDHI promoter and an *A. niger* eglA gene,
   (g) a *K. lactis* PGK promoter and a *T. reesei* cbhII gene,
   (h) a *K. lactis* AdhI promoter and a *N. crassa* cdt-1 gene,
   (i) a *K. lactis* Lac4 promoter and an *A. niger* egI gene,
   (j) a *K. lactis* AdhI promoter and a *T. reesei* cbhI gene,
   (k) a *K. lactis* Adh4 promoter and a *N. patriciarum* npabgs gene,
   (l) a *K. lactis* Lac4 promoter and a *T. aurantiacus* lpmo gene,
   (m) a *K. lactis* Lac4 promoter and a *M. thermophila* cdhI gene,
   (n) a *C. tropicalis* ICL promoter and a *T. reesei* cbhII gene,
   (o) a *K. lactis* AdhI promoter and a *T. aurantiacus* lpmo gene, and
   (p) an *S. cerevisiae* Adh1 promoter and a *M. thermophila* cdhI gene.

6. The engineered cell of claim 1, wherein the promoter and the gene in (ii) are selected from the group consisting of:
   (a) a *K. lactis* Lac4 promoter and a kanamycin resistance gene,
   (b) a *K. lactis* GapDHI promoter and a kanamycin resistance gene,
   (c) an *C. tropicalis* ICL promoter and an aureobasidin A resistance gene,
   (d) an *S. cerevisiae* ADH1 promoter and a kanamycin resistance gene,
   (e) an *S. cerevisiae* ADH1 promoter and a Zeocin resistance gene,
   (f) an *S. cerevisiae* ADH1 promoter and a hygromycin resistance gene,
   (g) an *S. cerevisiae* ADH1 promoter and an aureobasidin A resistance gene,
   (h) an *S. cerevisiae* ADH4 promoter and an aureobasidin A resistance gene, and
   (i) an *S. cerevisiae* ADH1 promoter and a blasticidin resistance gene.

7. The engineered cell of claim 1, wherein the cell contains:
   (1) a first nucleic acid molecule that contains the *K. lactis* Lac4 promoter operably linked to the KanMx gene,
   (2) a second nucleic acid molecule that contains the *S. cerevisiae* GapDHI promoter operably linked to the *T. reesei* egIII gene,
   (3) a third nucleic acid molecule that contains the *K. lactis* GapDHI promoter operably linked to the *T. reesei* cbhI gene,
   (4) a fourth nucleic acid molecule that contains the *K. lactis* AdhI promoter operably linked to the green fluorescent protein gene, and
   (5) a fifth nucleic acid molecule that contains the *S. cerevisiae* AdhI promoter operably linked to the *N. patriciarum* npabgs gene,
   (1)-(5) being adjacent to each other in the order of (1)-(2)-(3)-(4)-(5) in the 5' to 3' direction.

8. The engineered cell of claim 7, wherein (1)-(5) are inserted within the Lac4 promoter region of the parent *Kluyveromyces marxianus* cell of the engineered cell.

9. The engineered cell of claim 1, wherein the cell contains:
   (1) a first nucleic acid molecule that contains the *K. lactis* Lac4 promoter operably linked to the KanMx gene,
   (2) a second nucleic acid molecule that contains the *S. cerevisiae* GapDHI promoter operably linked to the *T. reesei* egIII gene,
   (3) a third nucleic acid molecule that contains the *S. cerevisiae* PGK promoter operably linked to the *T. reesei* cbhI gene,
   (4) a fourth nucleic acid molecule that contains the *K. lactis* GapDHI promoter operably linked to the *A. niger* eglA gene,
   (5) a fifth nucleic acid molecule that contains the *K. lactis* PGK promoter operably linked to the *T. reesei* cbhII gene,
   (6) a sixth nucleic acid molecule that contains the *K. lactis* AdhI promoter operably linked to the *N. crassa* cdt-1 gene, and
   (7) a seventh nucleic acid molecule that contains the *S. cerevisiae* AdhI promoter operably linked to the *N. patriciarum* npabgs gene,
   (1)-(7) being adjacent to each other in the order of (1)-(2)-(3)-(4)-(5)-(6)-(7) in the 5' to 3' direction.

10. The engineered cell of claim 9, wherein (1)-(7) are inserted within the Lac4 promoter region of the parent *Kluyveromyces marxianus* cell of the engineered cell.

11. The engineered cell of claim 1, wherein the cell contains:
   (1) a first nucleic acid molecule that contains the *K. lactis* Lac4 promoter operably linked to the *A. niger* egI gene,
   (2) a second nucleic acid molecule that contains the *S. cerevisiae* GapDHI promoter operably linked to the *T. reesei* egIII gene,
   (3) a third nucleic acid molecule that contains the *S. cerevisiae* PGK promoter operably linked to the *A. niger* eglA gene,
   (4) a fourth nucleic acid molecule that contains the *K. lactis* GapDHI promoter operably linked to the KanMx gene,
   (5) a fifth nucleic acid molecule that contains the *K. lactis* PGK promoter operably linked to the *T. reesei* cbhII gene,
   (6) a sixth nucleic acid molecule that contains the *K. lactis* AdhI promoter operably linked to the *T. reesei* cbhI gene, and
   (7) a seventh nucleic acid molecule that contains the *S. cerevisiae* AdhI promoter operably linked to the *N. patriciarum* npabgs gene, (1)-(7) being adjacent to each other in the order of (1)-(2)-(3)-(4)-(5)-(6)-(7) in the 5' to 3' direction.

12. The engineered cell of claim 11, wherein (1)-(7) are inserted within the Lac4 promoter region of the parent *Kluyveromyces marxianus* cell of the engineered cell.

13. The engineered cell of claim 1, wherein the cell contains:
   (1) a first nucleic acid molecule that contains the *K. lactis* Lac4 promoter operably linked to the *A. niger* egI gene,
   (2) a second nucleic acid molecule that contains the *S. cerevisiae* GapDH promoter operably linked to the *T. reesei* egIII gene,
   (3) a third nucleic acid molecule that contains the *S. cerevisiae* PGK promoter operably linked to the *A. niger* eglA gene,
   (4) a fourth nucleic acid molecule that contains the *S. cerevisiae* Adh4 promoter operably linked to the *T. reesei* cbhI gene,
   (5) a fifth nucleic acid molecule that contains the *C. tropicalis* ICL promoter operably linked to the *S. cerevisiae* AUR1 gene,
   (6) a sixth nucleic acid molecule that contains the *K. lactis* Adh4 promoter operably linked to the *N. patriciarum* npabgs gene,
   (7) a seventh nucleic acid molecule that contains the *K. lactis* PGK promoter operably linked to the *T. reesei* cbhII gene,
   (8) an eighth nucleic acid molecule that contains the *K. lactis* AdhI promoter operably linked to the *T. reesei* cbhI gene, and
   (9) a ninth nucleic acid molecule that contains the *S. cerevisiae* AdhI promoter operably linked to the *N. patriciarum* npabgs gene,
   (1)-(9) being adjacent to each other in the order of (1)-(2)-(3)-(4)-(5)-(6)-(7)-(8)-(9) in the 5' to 3' direction.

14. The engineered cell of claim 13, wherein (1)-(9) are inserted within the Lac4 promoter region of the parent *Kluyveromyces marxianus* cell of the engineered cell.

15. The engineered cell of claim 1, wherein the cell contains:
   (1) a first nucleic acid molecule that contains the *K. lactis* Lac4 promoter operably linked to the *A. niger* egI gene,
   (2) a second nucleic acid molecule that contains the *S. cerevisiae* GapDHI promoter operably linked to the *T. reesei* egIII gene,
   (3) a third nucleic acid molecule that contains the *S. cerevisiae* PGK promoter operably linked to the *A. niger* eglA gene,
   (4) a fourth nucleic acid molecule that contains the *K. lactis* GapDHI promoter operably linked to the KanMx gene,
   (5) a fifth nucleic acid molecule that contains the *K. lactis* PGK promoter operably linked to the *T. reesei* cbhII gene,
   (6) a sixth nucleic acid molecule that contains the *K. lactis* PGK promoter operably linked to the *T. reesei* cbhI gene,
   (7) a seventh nucleic acid molecule that contains the *S. cerevisiae* AdhI promoter is operably linked to the *N. patriciarum* npabgs gene,
   (8) an eighth nucleic acid molecule that contains the *K. lactis* Lac4 promoter operably linked to the *T. aurantiacus* lpmo gene, and
   (9) a ninth nucleic acid molecule that contains the *K. lactis* Lac4 promoter operably linked to the *M. thermophila* cdhI gene,
   (1)-(7) being adjacent to each other in the order of (1)-(2)-(3)-(4)-(5)-(6)-(7) in the 5' to 3' direction.

16. The engineered cell of claim 15, wherein (1)-(9) are inserted within the Lac4 promoter region of the parent *Kluyveromyces marxianus* cell of the engineered cell.

17. The engineered cell of claim 2, wherein the scaffold polypeptide of (iv) is a *C. thermocellum* cellulosomal scaffoldin.

* * * * *